(12) United States Patent
Dauvergne

(10) Patent No.: US 9,695,209 B2
(45) Date of Patent: Jul. 4, 2017

(54) SYNTHESIS OF AMPHIPHILIC CALIXARENE GLYCOSIDE DETERGENTS AND USE OF SAME FOR EXTRACTING AND STABILIZING NATIVE FUNCTIONAL MEMBRANE PROTEINS

(71) Applicant: CALIXAR, Lyons (FR)

(72) Inventor: Julien Dauvergne, Pierre Benite (FR)

(73) Assignee: CALIXAR, Lyons (FR)

( * ) Notice: Subject to any disclaimer, the term of this patent is extended or adjusted under 35 U.S.C. 154(b) by 0 days.

(21) Appl. No.: 15/303,039

(22) PCT Filed: Apr. 8, 2015

(86) PCT No.: PCT/EP2015/057544
§ 371 (c)(1),
(2) Date: Oct. 10, 2016

(87) PCT Pub. No.: WO2015/158575
PCT Pub. Date: Oct. 22, 2015

(65) Prior Publication Data
US 2017/0022241 A1    Jan. 26, 2017

(30) Foreign Application Priority Data

Apr. 14, 2014 (GB) .................................. 1406643.5

(51) Int. Cl.
| | | |
|---|---|---|
| *A61K 31/7004* | (2006.01) | |
| *C07D 249/06* | (2006.01) | |
| *C07D 249/08* | (2006.01) | |
| *C07H 15/04* | (2006.01) | |
| *C07H 15/26* | (2006.01) | |
| *C07H 13/04* | (2006.01) | |
| *C07H 13/12* | (2006.01) | |
| *C07H 15/24* | (2006.01) | |
| *C07K 1/14* | (2006.01) | |
| *C07K 14/00* | (2006.01) | |
| *C07K 14/705* | (2006.01) | |
| *B01D 11/02* | (2006.01) | |

(52) U.S. Cl.
CPC ......... *C07H 15/26* (2013.01); *B01D 11/0288* (2013.01); *C07H 13/04* (2013.01); *C07H 13/12* (2013.01); *C07H 15/04* (2013.01); *C07H 15/24* (2013.01); *C07K 1/145* (2013.01); *C07K 14/00* (2013.01); *C07K 14/70571* (2013.01)

(58) Field of Classification Search
CPC .............. A61K 31/7004; C07D 249/06; C07D 249/08; C07H 15/04
USPC ......... 514/23, 283; 536/1.11, 18.7; 548/255, 548/262.2
See application file for complete search history.

(56) References Cited

U.S. PATENT DOCUMENTS

2011/0144314 A1   6/2011   Coleman et al.
2012/0123088 A1   5/2012   Falson

FOREIGN PATENT DOCUMENTS

NO   2012/076934 A1   6/2012

OTHER PUBLICATIONS

Rima Matar-Merheb et al., "Structuring Detergents for Extracting and Stabilizing Functional Membrane Proteins", PLoS ONE, Mar. 31, 2011, vol. 6, Issue 3, 10 pages.

*Primary Examiner* — Raymond Henley, III
(74) *Attorney, Agent, or Firm* — Jordan IP Law, LLC; Todd A. Vaughn

(57) ABSTRACT

Amphiphilic calixarene glycoside compounds, the preparation of such compounds, and the use of such compounds for selectively extracting, solubilizing and stabilizing membrane proteins.

17 Claims, 5 Drawing Sheets

Figure 1A:
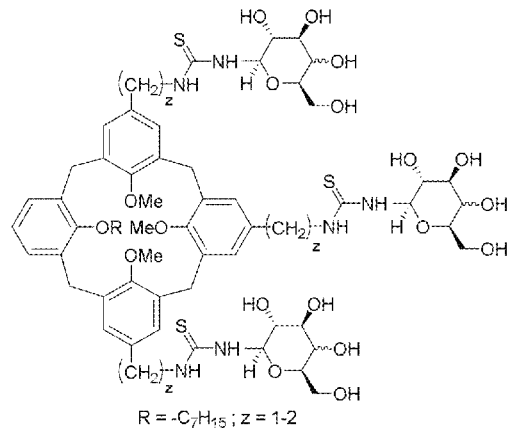

SYNTHESIS OF AMPHIPHILIC CALIXARENE GLYCOSIDE DETERGENTS AND USE OF SAME FOR EXTRACTING AND STABILIZING NATIVE FUNCTIONAL MEMBRANE PROTEINS

CROSS-REFERENCE TO RELATED APPLICATIONS

The present application is a National Stage application of PCT International Application No. PCT/EP2015/057544 (filed on Apr. 8, 2015), under 35 U.S.C. §371, which claims priority to Great Britain Patent Application No. GB 1406643.5 (filed on Apr. 14, 2014), which is hereby incorporated by reference in its complete entirety.

TECHNICAL FIELD

The present invention relates to new amphiphilic calixarene glycoside compounds, their preparation, and their use for selectively extracting, solubilizing and stabilizing membrane proteins.

BACKGROUND

Membrane proteins such as G-Protein Coupled Receptor (GPCR), other receptor proteins, enzymes, transport proteins and ion channels or other transmembrane proteins or proteins anchored to the biological membrane play a major role in the functioning of a cell, especially in relation with its growth control, the regulation of physiological functions, signaling and mediation of cellular transfer [Almen, M. S et al.: "Mapping the human membrane proteome: a majority of the human membrane proteins can be classified according to function and evolutionary origin"; BMC Biology; 2009; 7; 50]. Membrane proteins are amphiphilic macromolecules having hydrophilic and hydrophobic regions which across one or several times the biological membrane. The hydrophobic regions of certain amino acids bear apolar side chains which are folded in a helix and b barrel forms. Each of these secondary structures representing a TransMembrane Domain (TMD) have the hydrophobic parts of their amino acid directed towards the outside of the a helix, and contract by weak non-covalent hydrophobic interactions with the aliphatic chains of the lipids constituting the biologic membrane of cell, bacteria or virus. The cohesion of membrane proteins is also provided by the charged polar heads of lipids which induce Coulombic forces with their hydrophilic loops localized in the extracellular regions [Eva Pebay-Peyroula: Biophysical Analysis of Membrane Proteins, Wiley-VCH Books, 2008].

It has been estimated that about 20 to 30% of the human genome codes for Integral Membrane Proteins (IMP) [J. Nilsson et al., Proteins: Struct., Funct., Genet., 2005, 60, 606] and more than 50% which are involved in signaling pathways in the most serious forms of human diseases such as cancer, Alzheimer's disease, diabetes or malaria, making them particularly promising targets for drug development [John P. Overington et al.: "How many drug targets are there?"; Nature Reviews Drug Discovery, 5, 993-996, 2006].

However, in spite of progress made during the past years, the quantity of three dimensionally resolved structures of membrane proteins only accounts for about 2% of the 92 000 structures that have been posted in the Protein Data Bank (PDB) in 2014.

Membrane proteins can include one or more subunits together with hydrophobic co-factors such as lipids, saccharides, peptides or proteins. For most biochemical and biophysical in vitro studies, membrane proteins need to be extracted from the lipid bilayer by using synthetic compounds such as detergents.

Detergents are amphiphilic compounds with a structure comprising both polar and apolar distinct domains which confer them a good solubility in water. Detergents have surfactant properties and are able to adsorb on interfaces.

Self-assembly of detergents is a well-defined phenomenon ruled by the hydrophobic effect [C. Tanford, <<The Hydrophobic Effect: Formation of Micelles and Biological Membranes>>, $1^{st}$ Ed., John Wiley & Sons, Inc., New York, 1973]. At low concentrations, the presence in solution of non-polar groups disturbs the hydrogen bonds network between water molecules, which constrains them to organize themselves around apolar parts of the detergents and allows their solubilization.

To minimize this unfavorable disturbance of water molecules, the detergents are exchanged between the solution and the surface of the water where they form a compact film which decreases the surface tension of water. The liquid surface becomes saturated with detergent molecules from a threshold concentration called the Critical Micellar Concentration (CMC). The further addition of detergent molecules induces a spontaneous self-assembly and forms aggregate assemblies in solution called micelles which are defined by a size, a shape and an aggregation number.

The role of detergent-based micelles is to disturb the constitutive lipids of membrane cells stabilizing membrane proteins and solubilizes them in Protein/Detergent Complexes (PDC) while maintaining their conformational states to certain extend.

Monomers of detergent insert into the lipid bilayer until achieving its saturation, cause fragmentation and formation of mixed lipid/detergent micelles by action of detergent/detergent cooperative interactions. Sufficient amounts of detergent dissolve entirely lipids of the bilayer which results to a phase transition from a lamellar to a micellar phase comprising mixed lipid/detergent micelles and solubilized PDCs where their transmembrane domains interact with the hydrophobic tails of detergents [Le Maire et al.: "Interaction of membrane proteins and lipids with solubilizing detergents", Biochimica Biophysica Acta (BBA)—Biomembranes, 2000, 1508, 86-111].

Solubilization of membrane proteins therefore requires the use of detergents able to extract them from biological membrane and able to maintain them in aqueous solution under a conformational form by reproducing an environment around the protein similar to biological membranes with aid of structuring detergents. This extraction process still presents a major challenge related to the difficulties at handling over an extended period of time membrane proteins that tend to form aggregates in aqueous solution [M. Caffrey, "Membrane protein crystallization", J. Structural Biology, 2003, 142, 108-132]. During this process, the dissociating properties of detergents tend to disrupt essential protein/protein and protein/lipid interactions inside the quaternary structure of proteins which are essential to keep a specific folding responsible of their biological functions. Solubilization within the micelles of the different subunits for oligomeric proteins, a removing of lipid cofactors stabilizing or an intrusion of detergent tails onto hydrophobic transmembrane regions can cause an improper folding and disabling of the protein [J. U. Bowie, Curr. Opin. Struct. Biol., 2001, 11, 397-402; C. Breyton et al., J. Biol. Chem., 1997, 272, 21892-21900].

In this context, many commercially available detergents lead to the denaturation and the aggregation of the membrane protein, which is often irreversible [G. Privé: "Detergents for the stabilization and crystallization of membrane proteins", Methods, 2007, 41, 388-397]. Although a wide range of detergents for membrane protein research are available, there is no such thing as a "universal detergent" suitable to all protein studies.

According to the nature of their polar heads, detergents are commonly classified as ionic, zwitterionic or neutral. The neutral class is often related as mild detergents which are less denaturing against membrane proteins.

Detergents used in membrane protein biochemistry to extract and purify membrane targets are mostly neutral detergents comprising glycoside groups in the polar part of the amphiphilic structure among the most commonly used include Dodecyl β-D-Maltopyranoside (DDM) and Octyl β-D-Glucoside (OG).

Working on this basis, the scientific community has developed a new kind of amphiphilic topologies with glycoside residues in the polar part different from the conventional linear head/tail detergents [Popot, J.-L., Annu. Rev Biochem. 2010, 79, 737-775] such as the branch-chained maltoside detergents [Qinghai Zhang, "Design, Synthesis, and Properties of Branch-Chained Maltoside Detergents for Stabilization and Crystallization of Integral Membrane Proteins: Human Connexin 26", Langmuir, 2010, 26, 11, 8690-8696], nonionic amphipols [Bazzacco, P. et al., "Trapping and Stabilization of Integral Membrane Proteins by Hydrophobically Grafted Glucose-Based Telomers", Biomacromolecules, 2009, 10, 3317-3326], fluorinated surfactants [Breyton, C. et al., "Micellar and biochemical properties of (hemi)fluorinated surfactants are controlled by the size of the polar head", Biophys. J., 2009, 97, 1077-1086], amphiphilic tripods [Chae, P. S et. al., ChemBioChem, 2008, 9, 1706-9], steroidal facial amphiphiles [Lee, S. C. et al., "Steroid-based facial amphiphiles for stabilization and crystallization of membrane proteins", Proc. Natl. Acad. Sci. U.S.A., 2013, doi:10.1073/pnas.1221442110], tandem facial amphiphiles [Chae, P S; et al., J Am. Chem. Soc. 2010, 132, 16750-16752], maltose neopentyl-glycol amphiphiles [Pil Seok Chae et al., "Maltose-neopentyl glycol (MNG) amphiphiles for solubilization, stabilization and crystallization of membrane proteins", Nature Methods, 2010, 7, 1003-1008], glucose-neopentyl glyco amphiphiles [Chae, P. S. et al. "Glucose-Neopentyl Glycol (GNG) amphiphiles for membrane protein study", Chem. Commun., 2013, 49, 2287-2289], Chae's Glyco-Triton detergents [Chae, P. S. et al. <<Carbohydrate-containing Triton X-100 analogues for membrane protein solubilization and stabilization>>, Mol. BioSyst., 2013, 9, 626] and steroidal glyco-diosgenin amphiphiles [Chae, P. S. et al., "A New Class of Amphiphiles Bearing Rigid Hydrophobic Groups for Solubilization and Stabilization of Membrane Proteins", Eur. J. Chem., 2012, 18, 9485-9490]. Recently, a novel class of anionic detergents based on a rigid calixarene structure has been developed which allows to extract, solubilize, stabilize and purify a wide range of membrane proteins while conserving their native three-dimensional structure and maintaining them in a functional active form [Matar-Merheb, R. et al.: "Structuring Detergents for Extracting and Stabilizing Functional Membrane Proteins"; Plos One; 2011, 6]. This technology is also disclosed in the patent application US 2011/0144314 A1.

Calixarenes are macrocyclic compounds composed of phenolic units connected by an ortho-ortho methylene bridge forming a hydrophobic cavity that is capable of forming inclusion complexes with a variety of molecules [C. D. Gutsche; "Calixarenes"; Accounts of Chemical Research; 1983; 16; 161-170]. Some calixarenes have already been characterized, in particular the tetramers, hexamers and octamers as well as several calixarenes having an odd number of rings in their molecule. Calixarenes have found several applications in industry and are applied for example in enzyme mimetics, non-linear optics, ion sensitive electrodes or sensors, and more particularly in selective extraction of membrane proteins. In the latter case, calixarenes have been described in the patent application US 2011/144 314 A1 and US 2012/123088 A1.

These molecules have a cyclic platform comprising of four phenol units onto which is grafted a hydrophobic part on the lower rim and hydrophilic parts on the upper rim. The hydrophobic part is composed of a single aliphatic chain varying in length from one to sixteen carbon atoms. The hydrophilic part consists of three carboxylate groups.

It is relatively well established that membrane proteins display a higher level of basic residues at the cytosol-membrane interface creating an enrichment of positive charges on the intracellular membrane interface [Von Heijne, G.: "Membrane protein structure prediction: Hydrophobicity analysis and the positive-inside rule"; J. Molecular Biology, 1992, 225, 487-494]. Moreover, membrane proteins have a higher aromatic residue content localized at the membrane-water interface on their a-helical transmembrane segments which plays an important role to the assembly folding and stability [Hong, H. et al., "Role of Aromatic Side Chains in the Folding and Thermodynamic Stability of Integral Membrane Proteins"; J. Am. Chem. Soc., 2007, 129, 8320-8327].

Hence, these calixarene detergents confer a better packing of the transmembrane domains of extracted/purified membrane proteins and closer to that imposed by lipids in a bilayer membrane environment in comparison to that obtained by conventional detergents. Due to their structural pattern and higher rigidity, these detergents significantly improve stabilization of membrane proteins at several levels: (a) by allowing an efficient covering of hydrophobic transmembrane domains with aliphatic chains; (b) by establishing electrostatic interactions at the intracellular cytosol interface between positively charged amino acids on membrane protein loops and negatively charged carboxylate groups of the detergents and thus generating a salt bridges network in close proximity around the protein, and (c) by establishing a strong adsorption on hydrophobic domains by means of π-stacking interactions between phenolic components of the calixarene core and aromatic amino acid residues located at the interfaces.

Calixarenic detergents have demonstrated their usefulness for extracting and stabilizing a range of both eukaryotic and prokaryote membrane proteins such as ABC transporters from *Bacillus subtilis* expressed in *Escherichia Coli*, GPCR Class I from yeast, Human Receptors from HEK cells and viral proteins [A. Jawhari. et al.: "Native and full length membrane protein isolation for Drug Discovery"; 12th annual Drug Discovery on Target Conference, Boston; September 2013]. Despite the effectiveness and potential of these calixarene compounds, some of the target membrane proteins were not fully active after solubilization and/or cannot be solubilized. That is why the present inventors wanted to design other compounds that can complement the previous ones for improving the solubilization rate and/or the functionality conservation of membrane proteins.

SUMMARY

The first and major object of the present invention is to provide a family of calixarene glycoside compounds which enable the selective solubilization of membrane proteins while preserving their native three-dimensional structure.

Another object of the present invention is to provide a family of calixarene glycoside compounds which enable the selective solubilization of membrane proteins while preserving their native function.

Another object of the present invention is to provide a family of calixarene glycoside compounds which enable the selective stabilization of solubilized and/or purified membrane proteins while preserving their native function.

Another object of the present invention is to provide a family of calixarene glycoside compounds which enable the selective stabilization of solubilized and/or purified membrane proteins while preserving their native three-dimensional structure.

Another object of the present invention is a method for selectively extracting membrane proteins comprising a stage which consists of contacting an aqueous solution of the membrane protein to be extracted with at least one calixarene of the present invention.

These and other objects are met by a calixarene compound according to formula (Ia):

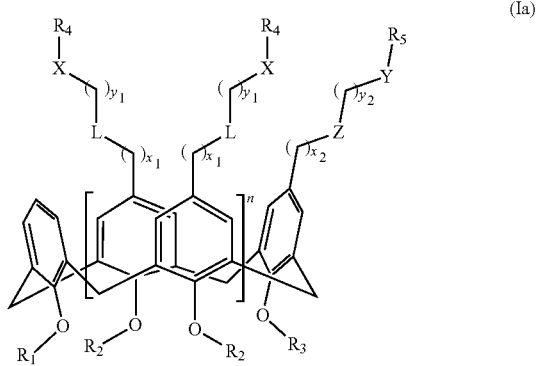

wherein:
n is an integer equal to 1;
R1 represents a linear or branched C(1-16) alkyl group;
R2 represents an hydrogen atom or a methyl group;
R3 is identical to R1 or R2 group;
R4 represents a saccharide residue, in which hydroxyl groups are not protected;
R5 is identical to R4 or is absent;
L is a linker, which is selected from the group consisting of 1,2,3-triazole function, amide function, thiourea function or is absent;
Z is identical to L or absent;
$0 \leq x1 \leq 3$, wherein x1 is an integer;
$0 \leq y1 \leq 3$, wherein y1 is an integer;
x2 is identical to x1 or equal to 0;
y2 is identical to y1 or equal to 0;
X=O, S or absent;
Y is identical to X or is absent.

An equivalent representation of formula (Ia) is formula (I):

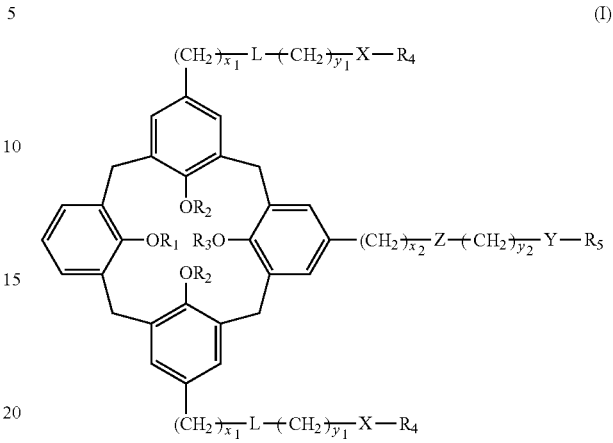

wherein:
R1 represents a linear or branched C(1-16) alkyl group;
R2 represents a hydrogen atom or a methyl group;
R3 is identical to R1 or R2 group;
R4 represents a saccharide residue, in which hydroxyl groups are not protected;
R5 is identical to R4, or is absent;
L is a linker, which is selected from the group consisting of 1,2,3-triazole function, amide function, thiourea function, or is absent;
Z is identical to L, or is absent;
$0 \leq x1 \leq 3$, wherein x1 is an integer;
$0 \leq y1 \leq 3$, wherein y1 is an integer;
x2 is identical to x1 or equal to 0;
y2 is identical to y1 or equal to 0;
X=O, S or absent;
Y is identical to X, or is absent.

According to one particular embodiment of the invention, the calixarene compound corresponds to formula (I), in which:
R1 represents a linear or branched C(1-16) alkyl group;
R2 represents a hydrogen atom or a methyl group;
R3 is identical to R1 or R2 group;
R4 represents a saccharide residue, in which hydroxyl groups are not protected, which is selected from the group of monosaccharides or disaccharides;
R5 is identical to R4, or is absent;
L is a linker, which is selected from the group consisting of 1,2,3-triazole function, amide function, thiourea function, or is absent;
Z is identical to L, or is absent;
$0 \leq x1 \leq 3$, wherein x1 is an integer;
$0 \leq y1 \leq 3$, wherein y1 is an integer;
x2 is identical to x1 or equal to 0;
y2 is identical to y1 or equal to 0;
X=O, S or absent;
Y is identical to X, or is absent.

According to one particular embodiment of the invention, the calixarene compound corresponds to formula (I), in which:
R1 represents a linear or branched C(1-16) alkyl group;
R2 represents a hydrogen atom or a methyl group;
R3 is identical to R1 or R2 group;

R4 represents a saccharide residue, in which hydroxyl groups are not protected, which is selected from the group consisting of glucosyl, mannosyl, galactosyl, maltosyl, lactosyl;

R5 is identical to R4, or is absent;

L is a linker, which is selected from the group consisting of 1,2,3-triazole function, amide function, thiourea function, or is absent;

Z is identical to L, or is absent;

$0 \leq x1 \leq 3$, wherein x1 is an integer;

$0 \leq y1 \leq 3$, wherein y1 is an integer;

x2 is identical to x1 or equal to 0;

y2 is identical to y1 or equal to 0;

X=O, S or is absent;

Y is identical to X, or is absent.

According to one particular embodiment of the invention, the calixarene compound corresponds to formula (I), in which:

R1 represents a linear or branched C(1-16) alkyl group;

R2, R3 represent a hydrogen atom or a methyl group;

R4, R5 represent a saccharide residue, in which hydroxyl groups are not protected, which is selected from the group consisting of glucosyl, mannosyl, galactosyl, maltosyl, lactosyl;

L is a linker, which is selected from the group consisting of 1,2,3-triazole function, amide function, thiourea function, or is absent;

Z is identical to L or is absent;

$0 \leq x1,2 \leq 3$, wherein x1,2 are an integer;

$0 \leq y1,2 \leq 3$, wherein y1,2 are an integer;

X represents an oxygen atom, a sulfur atom, or is absent.

Y represents an oxygen atom, a sulfur atom, or is absent.

According to one particular embodiment of the invention, the calixarene compound corresponds to formula (I), in which:

R1 corresponds to a linear or branched C(1-16) alkyl group;

R2, R3 are methyl;

R4, R5 represent a saccharide residue, in which hydroxyl groups are not protected, which is selected from the group consisting of glucosyl, mannosyl, galactosyl, maltosyl, lactosyl;

L is a linker, which is selected from the group consisting of 1,2,3-triazole function, amide function, thiourea function, or is absent;

Z is identical to L or is absent;

$0 \leq x1,2 \leq 3$, wherein x1,2 are an integer;

$0 \leq y1,2 \leq 3$, wherein y1 are an integer;

X represents an oxygen atom, a sulfur atom, or is absent;

Y represents an oxygen atom, a sulfur atom, or is absent.

According to one particular embodiment of the invention, the calixarene compound corresponds to formula (I), in which:

R1 corresponds to a linear or branched C(1-16) alkyl group;

R2, R3 are methyl;

R4, R5 represent a galactosyl group, in which hydroxyl groups are not protected;

L is a linker, which is selected from the group consisting of 1,2,3-triazole function, amide function, thiourea function, or is absent;

Z is identical to L or is absent;

$0 \leq x1,2 \leq 3$, wherein x1,2 are an integer;

$0 \leq y1,2 \leq 3$, wherein y1,2 are an integer;

X represents an oxygen atom, a sulfur atom, or is absent;

Y represents an oxygen atom, a sulfur atom, or is absent.

According to one particular embodiment of the invention, the calixarene compound corresponds to formula (I), in which:

R1 corresponds to a linear or branched C(1-16) alkyl group;

R2, R3 are methyl;

R4, R5 represent a galactosyl group, in which hydroxyl groups are not protected;

L, Z are absent;

$0 \leq x1,2 \leq 3$, wherein x1,2 are an integer;

$0 \leq y1,2 \leq 3$, wherein y1,2 are an integer;

X represents an oxygen atom, a sulfur atom, or is absent;

Y represents an oxygen atom, a sulfur atom, or is absent.

According to one particular embodiment of the invention, the calixarene compound corresponds to formula (I), in which:

R1 corresponds to a linear or branched C(1-16) alkyl group;

R2, R3 are methyl;

R4, R5 represent a glucosyl group, in which hydroxyl groups are not protected;

L is a linker, which is selected from the group consisting of 1,2,3-triazole function, amide function, thiourea function, or is absent;

Z is identical to L or is absent;

$0 \leq x1,2 \leq 3$, wherein x1,2 are an integer;

$0 \leq y1,2 \leq 3$, wherein y1,2 are an integer;

X represents an oxygen atom, a sulfur atom, or is absent;

Y represents an oxygen atom, a sulfur atom, or is absent.

According to one particular embodiment of the invention, the calixarene compound corresponds to formula (I), in which:

R1 corresponds to a linear or branched C(1-16) alkyl group;

R2, R3 are methyl;

R4, R5 represent a glucosyl group, in which hydroxyl groups are not protected;

L, Z are a 1,2,3-triazole function;

$0 \leq x1,2 \leq 3$, wherein x1,2 are an integer;

$0 \leq y1,2 \leq 3$, wherein y1,2 are an integer;

X represents an oxygen atom, a sulfur atom, or is absent;

Y represents an oxygen atom, a sulfur atom, or is absent.

According to one particular embodiment of the invention, the calixarene compound corresponds to formula (I), in which:

R1, R3 correspond to a linear or branched C(1-16) alkyl group;

R2 represents an hydrogen atom or a methyl group;

R4 represents a maltosyl group, in which hydroxyl groups are not protected;

R5 is absent;

L is a linker, which is selected from the group consisting of 1,2,3-triazole function, amide function, thiourea function, or is absent;

Z is absent;

$0 \leq x1 \leq 3$, wherein x1 are an integer;

$0 \leq y1 \leq 3$, wherein y1 are an integer;

x2 and y2 are equal to 0;

X=O, S or is absent;

Y is absent.

According to one particular embodiment of the invention, the calixarene compound corresponds to formula (I), in which:

R1, R3 correspond to a linear or branched C(1-16) alkyl group;

R2 represents a methyl;

R4 represents a maltosyl group, in which hydroxyl groups are not protected;

R5 is absent;

L is a linker, which is selected from the group consisting of 1,2,3-triazole function, amide function, thiourea function, or is absent;

Z is absent;

$0 \leq x1 \leq 3$, wherein x1 are an integer;

$0 \leq y1 \leq 3$, wherein y1 are an integer;

x2 and y2 are equal to 0;

X=O, S or is absent;

Y is absent.

According to one particular embodiment of the invention, the calixarene compound corresponds to formula (I), in which:

R1, R3 correspond to a linear or branched C(1-16) alkyl group;

R2 represents a methyl;

R4 represents a maltosyl group, in which hydroxyl groups are not protected;

R5 is absent;

L is a 1,2,3-triazole;

Z is absent;

$0 \leq x1 \leq 3$, wherein x1 are an integer;

$0 \leq y1 \leq 3$, wherein y1 are an integer;

x2 and y2 are equal to 0;

X=O, S or is absent;

Y is absent.

Another object of the present invention is a method for selectively extracting, solubilizing and/or stabilizing membrane proteins, comprising a stage which consists of contacting membrane pellets containing one or more membrane proteins to be extracted with an aqueous solution containing at least one calixarene compound according to the invention.

The invention further provides methods of selectively extracting a membrane protein from a lipid bilayer, e.g. a thin polar membrane made of two layers of lipid molecules, by contacting the lipid bilayer with at least one calixarene described herein in an aqueous solution to form a mixture, optionally in the presence of a buffer or other detergent, thereby forming an assembly of the calixarene compounds and the membrane protein extracted from the lipid bilayer. The assembly can then be separated from the mixture to provide isolated and/or purified membrane protein. The invention further provides methods of selectively stabilizing the membrane protein by contacting the isolated and/or purified membrane protein with at least one calixarene described herein in an aqueous solution. More particularly, the method is characterized in that the membrane protein is a protein selected from the group comprising: (a) the transport proteins, preferably multi-drug efflux transporter selected from the group comprising the Acridine resistance protein B (AcrB) and a proton pump from the group comprising the bacteriorhodopsin (bR); (b) the ion channels, preferably an M2 proton channel selected from the group comprising the influenza virus matrix protein 2 (M2); or (c) G protein-coupled receptors (GPCRs), preferably adenosine A2A receptor; or (d) enzymes; or (e) glycoproteins.

According to one particular implementation mode of the invention, the stage of contacting membrane pellets containing one or more membrane proteins to be extracted with an aqueous solution containing at least one calixarene according to the invention is effected at a pH ranging from 6 to 9.

According to one particular implementation mode of the invention the stage of contacting membrane pellets containing one or more membrane proteins to be extracted with an aqueous solution containing at least one calixarene according to the invention is effected at a temperature ranging from 4 to 25° C.

According to one particular implementation mode of the invention the stage of contacting membrane pellets containing one or more membrane proteins to be extracted with an aqueous solution containing at least one calixarene according to the invention is carried out at a calixarene concentration ranging from 10-6 to 10-3 M.

Another object of the present invention is a method for producing a solution of membrane proteins comprising the extraction of membrane proteins with at least one calixarene compound according the invention, and the separation of said membrane proteins extracted with said calixarenes, preferably by centrifugation.

According to one particular implementation mode of the invention the stage of contacting solubilized or purified membrane proteins with a buffer solution containing at least one calixarene according to the invention is carried out at a calixarene concentration ranging from 10-6 to 10-3 M.

Another object of the present invention is a method of solubilizing and/or stabilizing a membrane protein, by contacting membrane pellets containing one or more membrane proteins to be extracted with an aqueous solution containing at least one calixarene according to the invention, and optionally heating the membrane protein and the membrane pellets, thereby forming a solubilized or stabilized of the membrane protein.

Another object of the present invention is a method for producing a solution of membrane proteins comprising the extraction of membrane proteins with at least one calixarene compound according to the invention, and the separation of said membrane proteins extracted with said calixarenes, preferably by centrifugation.

DRAWINGS

FIGS. 1a) to 1f) show preferred embodiments of calixarene compounds corresponding to formula (I) according to the present invention.

FIG. 1a) corresponds to a calixarene compound of formula (I) wherein R1 is a heptyl group; R2 and R3 are methyl groups; R4 and R5 are the same and represent a galactosyl or glucosyl group; X,Y are absent; L,Z are a thiourea function; x1,2=z=1 to 2, y1,2=0.

Figure 1B:
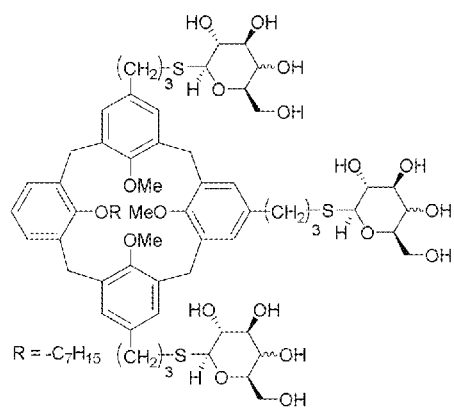

FIG. 1b) corresponds to a calixarene compound of formula (I) wherein R1 is a heptyl group; R2 and R3 are methyl groups; R4 and R5 are the same and represent a galactosyl or glucosyl group; wherein X,Y=S; L,Z are absent; and x1+y1=x2+y2=3.

Figure 1C:
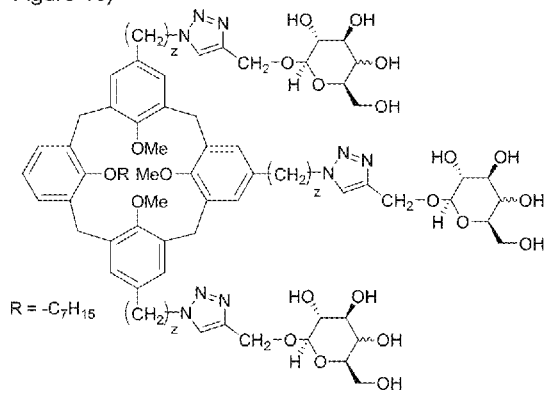

FIG. 1c) corresponds to a calixarene compound of formula (I) wherein R1 is a heptyl group; R2 and R3 are methyl groups; R4 and R5 are the same and represent a galactosyl or glucosyl group; X,Y=O; L,Z are a 1,2,3-triazole function x1,2=z=1 to 2 and y1,2=1.

Figure 1D:
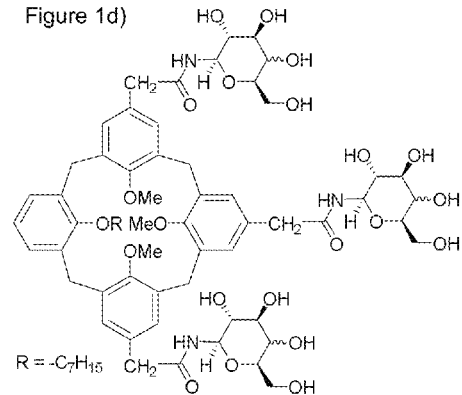

FIG. 1d) corresponds to a calixarene compound of formula (I) wherein R1 is a heptyl group; R2 and R3 are methyl groups; R4 and R5 are the same and represent a galactosyl or glucosyl group; X,Y are absent; L,Z are an amide function; and x1,2=1 and y1,2=0.

Figure 1E:
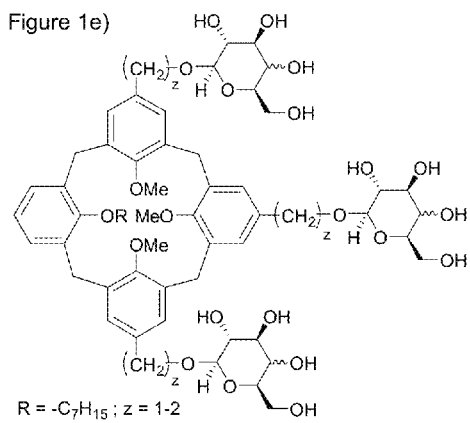

FIG. 1e) corresponds to a calixarene compound of formula (I) wherein: R1 is a heptyl group; R2 and R3 are methyl groups; R4 and R5 are the same and represent a galactosyl or glucosyl group; wherein X,Y=O; L,Z are absent; and x1+y1=x2+y2=z=1 to 2.

Figure 1F:
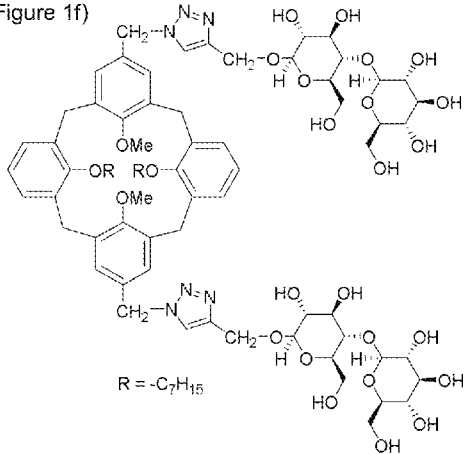

FIG. 1f) corresponds to a calixarene compound of formula (I) wherein: R1 is a heptyl group; R2 and R3 are methyl groups; R4 and R5 are the same and represent a maltosyl group; wherein X,Y=O; L,Z are a 1,2,3-triazole function; x1,2=1 and y1,2=1.

Figure 2:
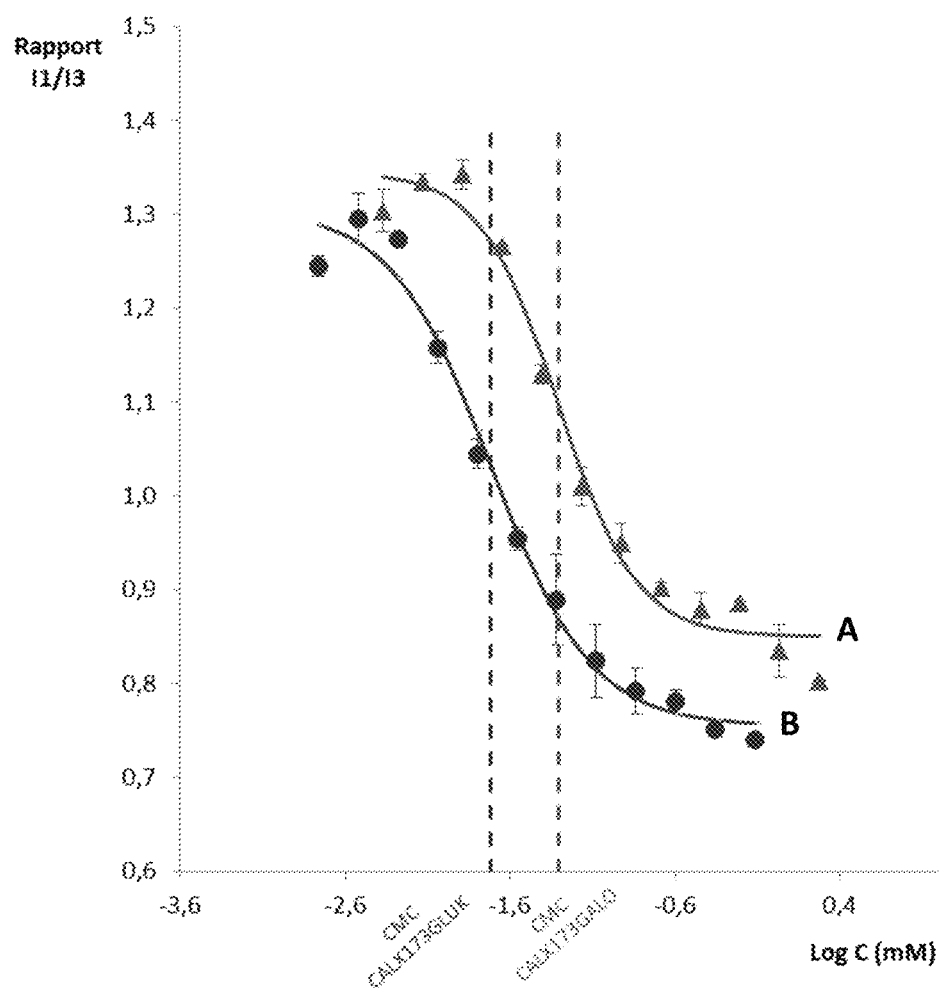

FIG. 2 shows decreasing sigmoid of the Boltzmann type obtained by spectrofluorimetric method using pyrene as a fluorescence probe for determining the critical micelle concentration. The x-axis represents the "log" concentration of calixarenes; y-axis represents the ratio of intensity of the first (I1 at 373 nm) and third peaks (I3 at 384 nm) of pyrene. The sigmoid "A" is related to CALX173GALO calixarene dissolved in MilliQ® H2O, and the sigmoid "B" is related to CALX173GLUK calixarene dissolved in MilliQ® H2O.

Figure 3A:
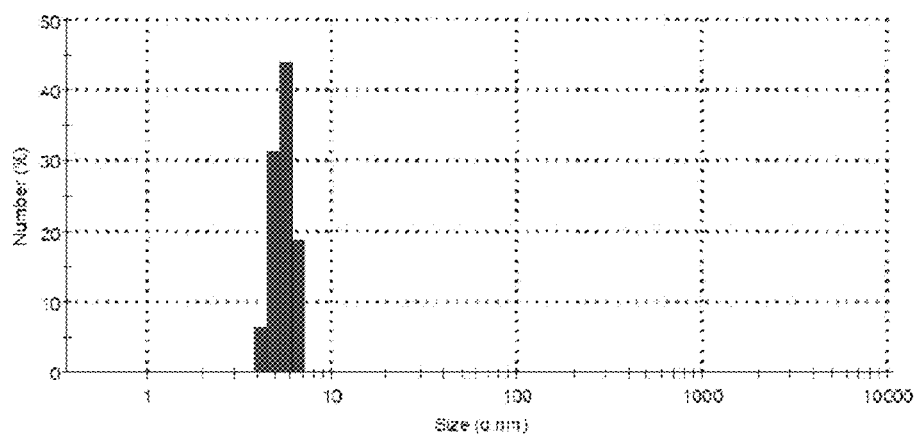

FIGS. 3a) and 3b) are two diagrams showing the average particle size obtained by DLS (Dynamic Light Scattering) analysis of CALX173GALO compound (FIG. 3a) and CALX173GLUK compound (FIG. 3b) at respectively 0.47 and 0.08 mM.

Figure 4A:
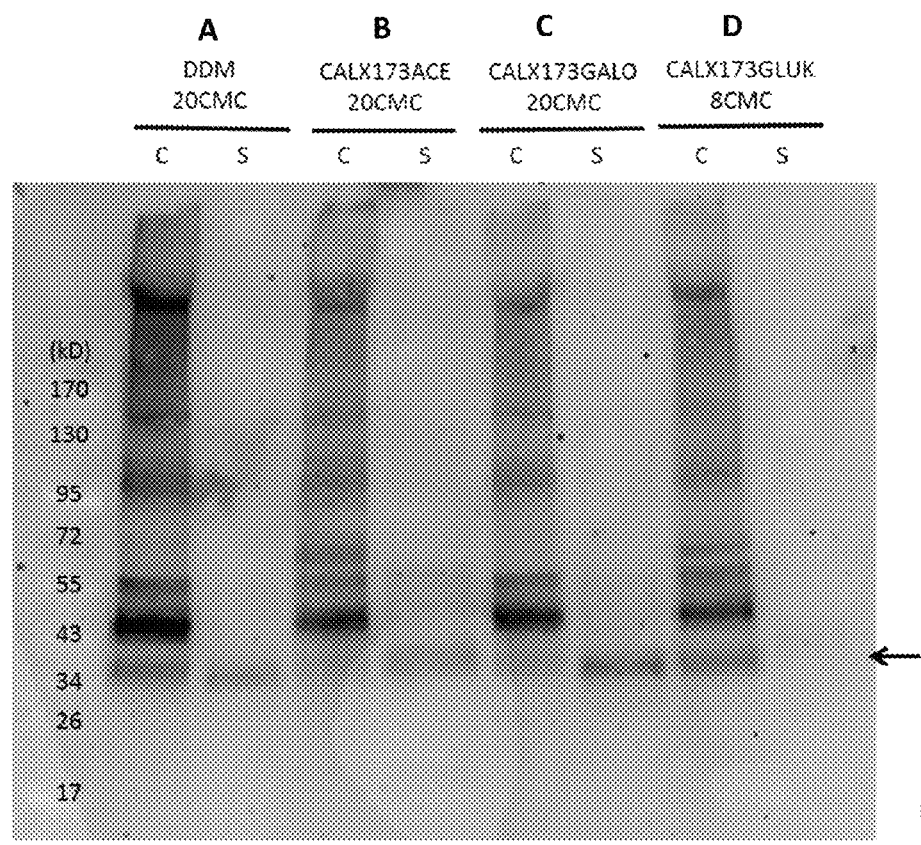
Figure 4B:
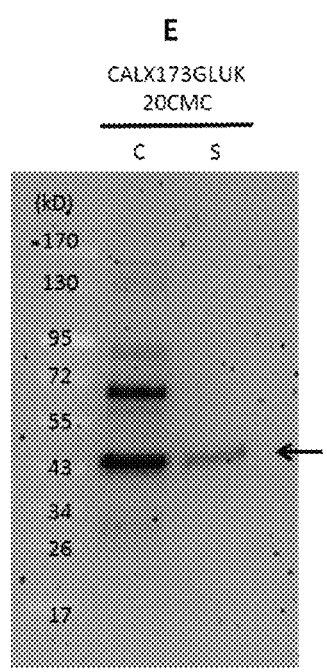

FIGS. 4a) and 4b) shows the test of solubilization of A2A membrane protein with CALX173GALO, and CALX173GLUK calixarenes of the present invention, and also known detergents, e.g. n-dodecyl-β-D-maltopyranoside (DDM, CMC (H2O)=0.17 mM [VanAken, T. et al, Alkyl glycoside detergents: synthesis and applications to the study of membrane proteins, 1986, Meth. Enzymol., 125, 27-35]) and 25-heptyloxy-26,27,28-tris(hydroxyl)calix-[4]-arene-5,11,17-tris(acetic acid) sodium salt (called "CALX173ACE", CMC (H2O)=2.5 mM).

Figure 5:
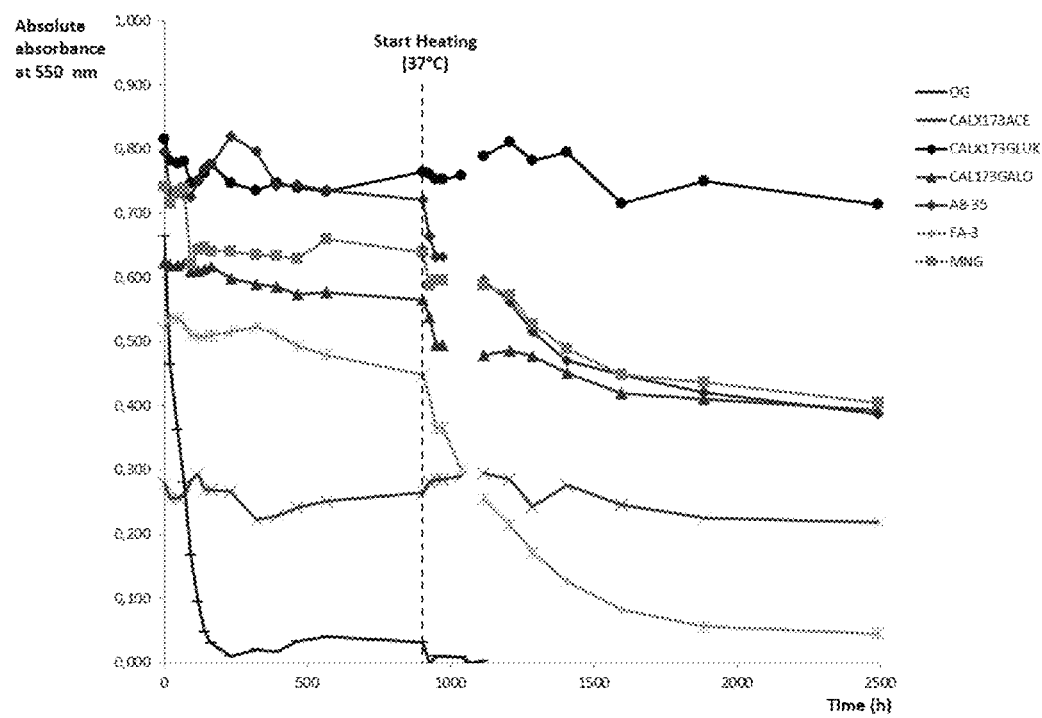

FIG. 5 shows the effect of stabilization of membrane protein bR over the time at room temperature then 37° C. in various detergent conditions (OG, CALX173ACE, CALX173GALO, CALX173GLUK, amphipol A8-35, FA-3 and MNG)

DESCRIPTION

1. Definitions

In the sense of the present invention "alkyl" is understood to mean a linear, branched or cyclic, saturated, possibly substituted monovalent hydrocarbonradical. An "alkyl in C1 to C16" is an alkyl comprising 1 to 16 carbon atoms; this comprises in particular the methyl and ethyl groups as well as linear and branched propyl, butyl, isobutyl, pentyl, hexyl, heptyl, octyl, nonyl, decyl, undecyl, dodecyl, tridecyl, tetradecyl, pentadecyl and hexadecyl groups. The alkyl group can possibly be substituted with one or more monovalent hetero atoms selected from the group of O, S, N, P atoms, and can therefore carry various function such as —OH, —NO2, —N2, —SO2(OH).

In the context of the present invention, the term "pharmaceutically acceptable salts" comprises the salts prepared with non-toxic acids or bases, depending on the substituents present on the compounds. When the compounds of the invention contain acidic functions, the corresponding salts can be obtained by addition of an organic or inorganic base to the compound in neutralized form possibly in the presence of a preferably inert solvent. Examples of addition salts of a base can be the sodium, potassium, calcium, ammonium, amino (organic), or magnesium salts. When the compounds of the invention contain basic functions, the corresponding salts can be obtained by addition of an organic or inorganic acid possibly in a preferably inert solvent. Examples of inorganic acid addition salts can be the hydrochloride, hydrobromide, nitrate, carbonate, monohydrogen carbonate, phosphate, monohydrogen phosphate, dihydrogen phosphate, sulfate, monohydrogen sulfate or hydriodide salts. Examples of organic acid addition salts can be the acetate, propionate, isobutyrate, maleate, malonate, benzoate, succinate, suberate, fumarate, lactate, mandelate, phthalate, benzenesulfonate, p-tolylsulfonate, citrate, tartrate or methanesulfonate salts.

In the sense of the present invention a saccharide residue refers to a sugar moiety, such as a monosaccharide, disaccharide, oligosaccharide or polysaccharide. Typical monosaccharides include allose, altrose, glucose, mannose, gulose, idose, galactose, or talose. Typical disaccharides include galactose, lactose, maltose, sucrose, trehalose, and cellobiose. Disaccharides can have any suitable linkage between the first and the second unit of the dissaccharide. Other suitable saccharides include glucuronic acid, sorbase, ribose, and the like. The saccharides can be linked to formula (I) via their anomeric oxygen, or to any other available hydroxyl group. Depending on the context, as would be understood by one of skill in the art, the saccharide can include the oxygen that links it to another group, or exclude the oxygen that links it to another group.

In the sense of the present invention "membrane protein" is understood to mean a protein associated with biological membranes or artificial membranes (such as Virus-Like-Particles or liposomes), in other words either anchored, or integral, and not free for diffusion in aqueous media and unstable in those media, and also soluble proteins which are instable in those media. Among the membrane proteins, for example the proteins of plasma membranes and the proteins of intracellular membranes (such as for example the proteins of mitochondrial, nuclear and lysosomal membranes) can be cited. The membrane proteins are often classified on the basis of the structures which enable them to interact with the membranes and the manner in which these structures fit together. The membrane proteins can be polytopic proteins or monotopic proteins.

In the sense of the present invention, "aqueous solution of the membrane protein" is understood to mean an aqueous solution comprising one or more membrane protein(s). For example, this can be a suspension or a dispersion, wherein the proteins can be in a non-dissolved or non-diffuse form or can for example be combined with a biological membrane fraction.

The following abbreviations are used:
Ac=Acetyle Bz=Benzoyle
tBu=tert-Butyle Me=Methyle
Et=Ethyle Ph=Phenyle Tf=Triflate

2. Description

The present invention provides a family of calixarene compounds defined by formula (I):

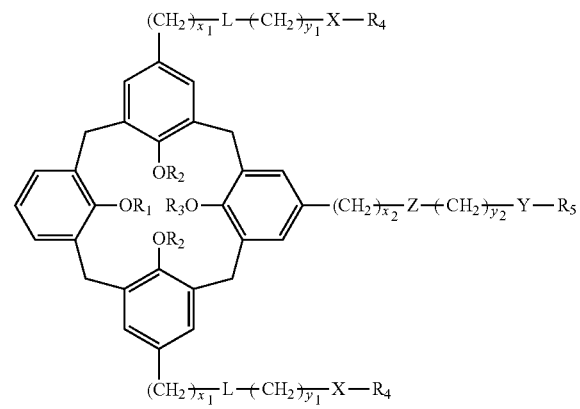

Formula (I)

wherein:

R1 represents a linear or branched C(1-16) alkyl group;
R2 represents an hydrogen atom or a methyl group;
R3 is identical to R1 or R2 group;
R4 represents a saccharide residue, in which hydroxyl groups are not protected;
R5 is identical to R4 or absent;
L is a linker, which is selected from the group consisting of 1,2,3-triazole function, amide function, thiourea function or may be absent;
Z is identical to L or absent;
0≤x1≤3, wherein x1 is an integer;
0≤y1≤3, wherein y1 is an integer;
x2 is identical to x1 or equal to 0;
y2 is identical to y1 or equal to 0;
X=O, S or absent;
Y is identical to X or absent.

According to one particular embodiment of the invention, the calixarene compound corresponds to formula (I), in which:

R1 represents a linear or branched C(1-16) alkyl group;
R2 represents an hydrogen atom or a methyl group;
R3 is identical to R1 or R2 group;
R4 represents a saccharide residue, in which hydroxyl groups are not protected, which is selected from the group of monosaccharides or disaccharides;
R5 is identical to R4 or absent;
L is a linker, which is selected from the group consisting of 1,2,3-triazole function, amide function, thiourea function or may be absent;
Z is identical to L or absent;
0≤x1≤3, wherein x1 is an integer;
0≤y1≤3, wherein y1 is an integer;
x2 is identical to x1 or equal to 0;
y2 is identical to y1 or equal to 0;
X=O, S or absent;
Y is identical to X or absent.

More precisely, on account of their chemical formula, the calixarenes of formula (I) have a molecular geometry in the shape of a cone or truncated cone, in which the flared region is hydrophilic whereas the tail is hydrophobic. This particular shape of the calixarenes of formula (I) enables the formation of micelles, which facilitates the transfer of the proteins from a membrane environment towards an aqueous medium, and which also promote the conservation of their three-dimensional structure and hence of their biological activity.

The introduction of saccharide units in a molecule can be carried out by a glycosylation reaction via an alcohol function. These calixarene compounds as illustrated in FIG. 1e (called here "CALX1N3GALO" where N is an integer from 1 to 16 corresponding to the length of the alkyl chain) are accessible via the glycosylation reaction as represented in detail in Reaction Scheme 1. Reagents and reaction conditions are mentioned as examples, which do not limit the scope of the invention.

Reaction Scheme 1: Preparation of CALX173GALO (5)

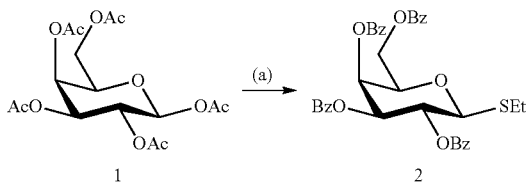

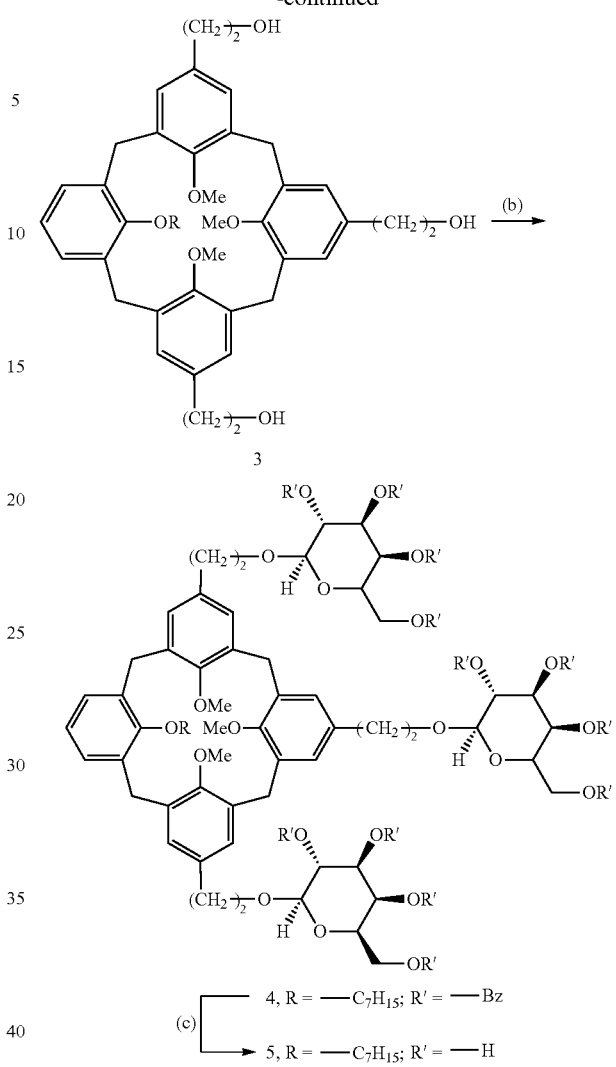

Reagents and Conditions in Relation with Reaction Scheme 1:

(a) CH2Cl2/BF3.Et2O, EtSH, 2 h at room temperature, then tBuOK/MeOH, 2 h, room temperature, then BzCl/Pyridine, 1 h to room temperature; Yield=87%, (b) Cu(OTf)2/MeCN, Argon/3A MS (Molecular Sieve), 2, 2 h at room temperature, then (c) MeOH/CH2Cl2/MeONa, pH 12, Argon, 16 h at room temperature; Yield=20%.

CAL173GALO (5) can be synthesized by a glycosylation reaction between the calix-[4]-arene triol intermediate 3 and the derivative ethyl 2,3,4,6-tetra-O-benzoyl-1-thio-b-D-galactopyranoside 2 followed by the removal of the benzoyl protecting groups by a transtesterification reaction. The thioethyl tetrabenzoyl-b-D-galactopyranoside 2 was synthesized according to the literature [Dondoni, A. et al, Synthesis and Properties of O-Glycosyl Calix[4]Arenes (Calixsugars), Chem. Eur. J., 1997, 3, 1774-1782]. The calix-[4]-arene triol 3 can be synthesized from 4-tert-Butylphenol 6 (CAS Number 98-54-4) as represented in Reaction Scheme 2. Reagents and reaction conditions are mentioned as examples, which do not limit the scope of the invention.

Reaction Scheme 2: Preparation of intermediate calix-[4]-arene 3
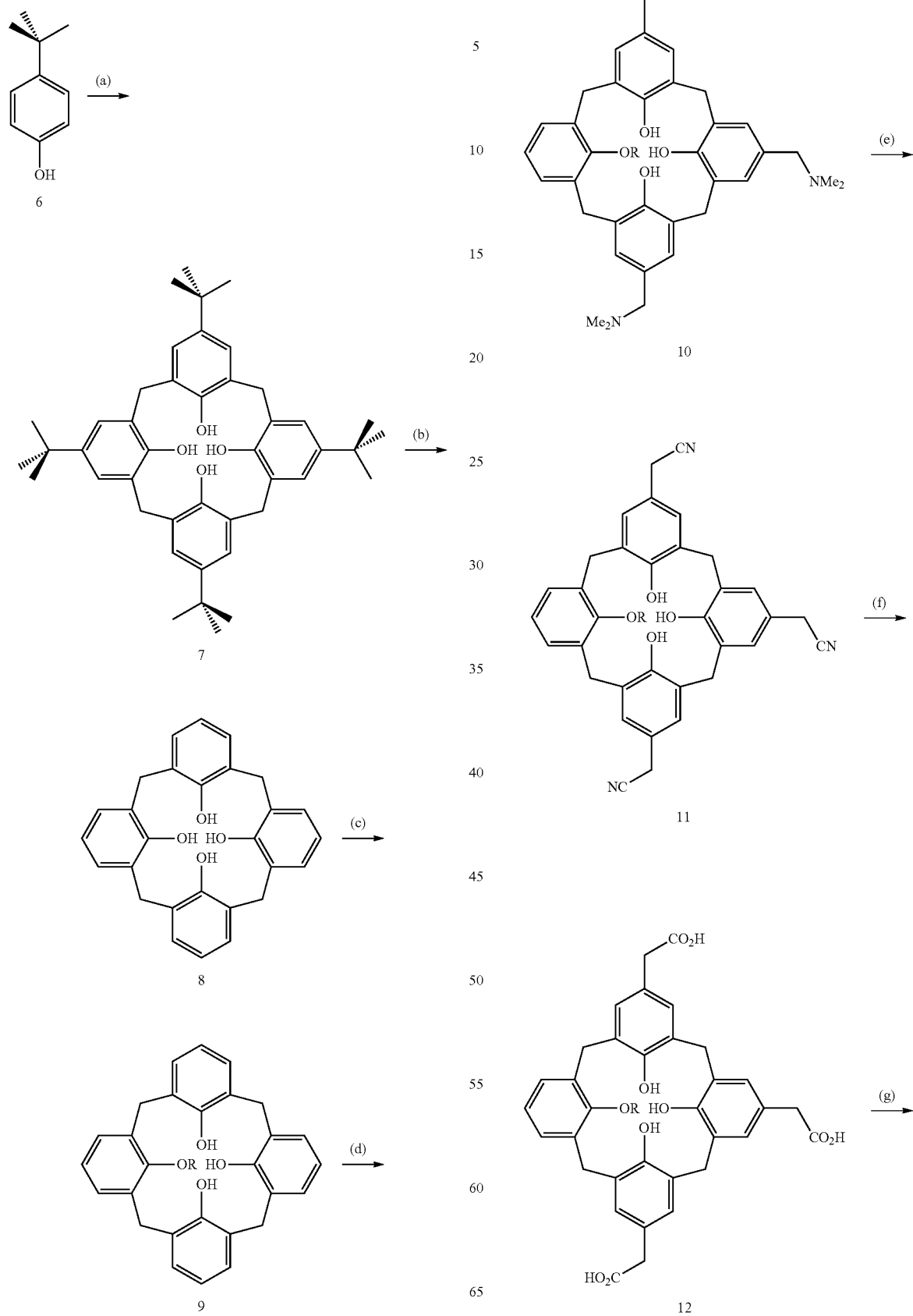

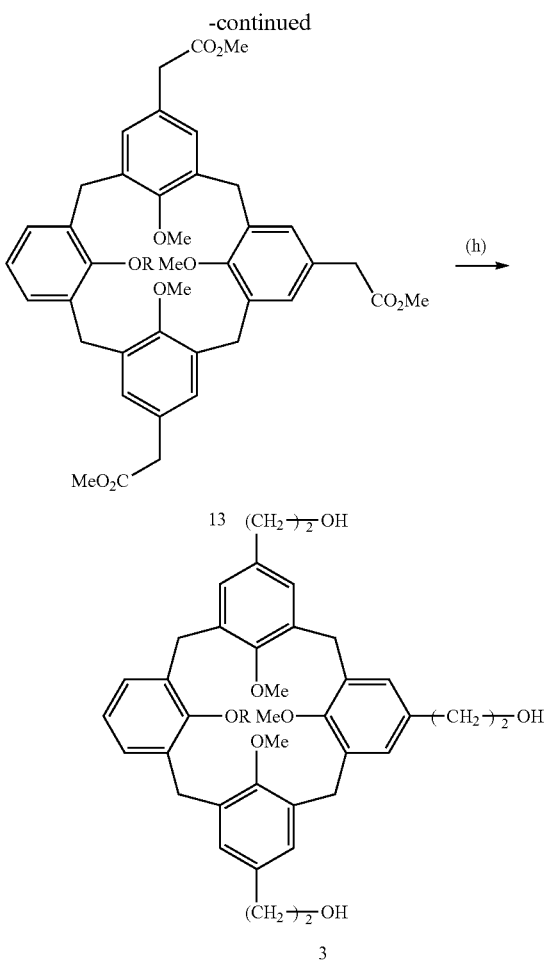

Reagents and Conditions in Relation with Reaction Scheme 2:

(a) NaOH/HCHO, 2 h at 120° C., then diphenyl ether, 3 h at 250° C.; Yield=52%,
(b) AlCl3/PhCH3, PhOH, 3 h at room temperature; Yield=95%,
(c) C7H15I/NaHCO3, DMF, 5 days at 40° C.; Yield=75%,
(d) AcOH/Me2NH, HCHO/THF, 3 days at room temperature, quantitative,
(e) DMSO/MeI, argon, 30 min at 40° C. then NaCN, argon, 48 h at 80° C.; Yield=50%,
(f) KOH/H2O, EtOH, 3 days at 120° C.; Yield=75%,
(g) NaH (60%), DMF/MeI, 16 h at room temperature; Yield=80%,
(h) LiAlH4/THF, 2 h at room temperature; Yield=75%.

However, depending on the number of units to insert in the calixarene compound, the experimental conditions and more particularly the steric effects, it turns out that it can be difficult to introduce effectively all of saccharide units, which inevitably results in poor overall yields (see the 20% yield at glycosylation step for synthesis of CALX173GALO compounds), inefficient synthesis and formation of crude mixtures where it is difficult to purify compound of interest on large scale.

In order to overcome this problem, the inventors have developed another synthesis pathway to insert saccharide units in the calixarene-based platform.

More particularly, according to the invention, a 1,3-dipolar reaction, catalyzed by copper (I), between an alkyne and an azide (copper (I)-catalyzed alkyne-azide cycloaddition: CuAAC) represents a suitable method to inserting saccharide units in the calixarene-based platform. These calixarene compounds as illustrated in FIG. 1f (called here "CALX1N3GLUK" where N is an integer from 1 to 16 corresponding to the length of the alkyl chain) are accessible via the reaction sequence shown in Reaction Scheme 3. Reagents and reaction conditions are mentioned as examples, which do not limit the scope of the invention. CALX173GLUK 18 can be synthesized from the tris-azidopropyl-substituted calix-[4]-arene 16 and the propargyl 2,3,4,6-tetra-O-acetyl-β-D-glucopyranose 15 prepared according to the literature [Mereyala, H. B. & Gurrala, S. R., Carbohyd. Res., 1998, 307, 351-354].

Reaction Scheme 3: Preparation of CALX173GLUK 18

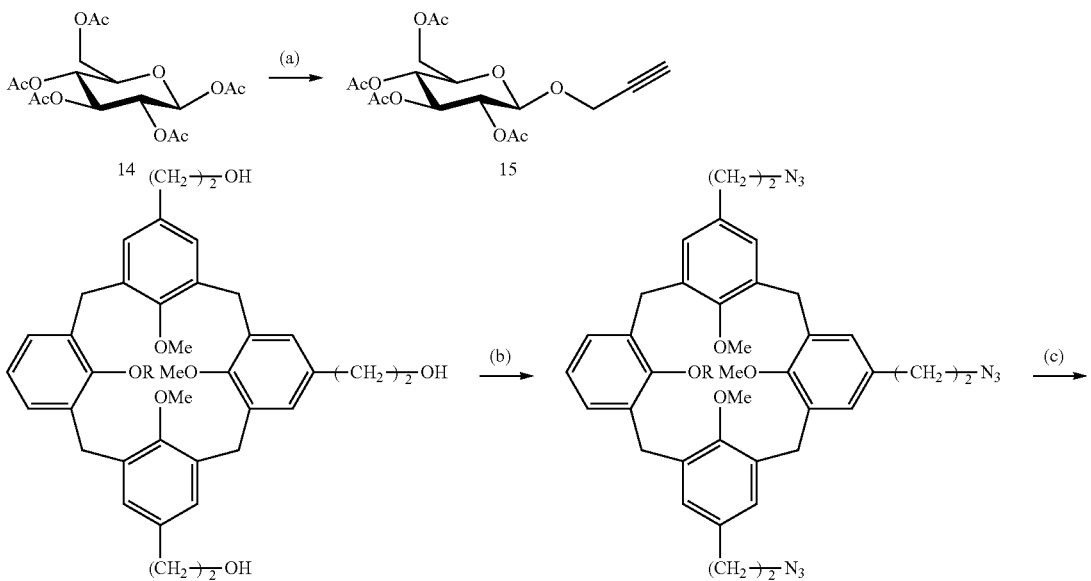

-continued

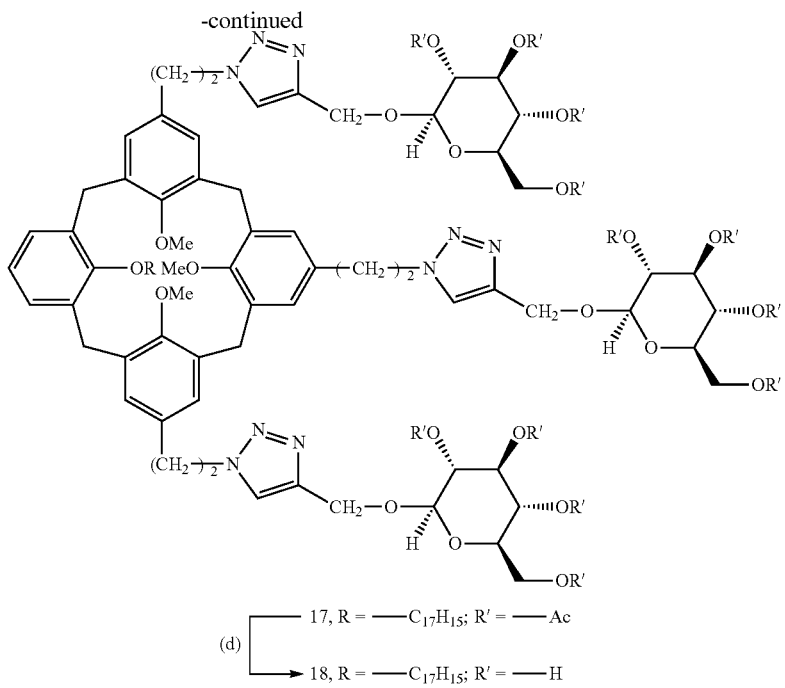

17, R = —C$_{17}$H$_{15}$; R' = —Ac (d)

18, R = —C$_{17}$H$_{15}$; R' = —H

Reagents and Conditions in Relation with Reaction Scheme 3:

(a) Propargyl alcohol, BF$_3$.Et$_2$O/CH$_2$Cl$_2$, 2 h at room temperature; Yield=90%, (b) DMF/NaN3, DBU/diphenylphosphoryl azide, 14 h at 120° C.; Yield=84%, (c) DMF/iPrEt2N, Argon, CuI/3A MS, 15, 4 h 30 at 90° C. then, (d) MeOH/CH2Cl2/MeONa; Yield=71%.

The bonding between the saccharide units and the calix-[4]-arene-based platform via aromatic 1,2,3-triazole rings may have a stabilizing effect, as the phenol rings of the calixarene. This effect can be explained by "π-stacking" interactions with hydrophobic aromatic residues of membrane proteins. Moreover, the distance of the saccharide units from the calixarene-based platform provides more freedom of movement to the saccharide residues, which allows them to take the most favorable conformation to stabilize a membrane protein.

The method of the invention enables the extraction of a given protein, selectively relative to other membrane proteins, in particular by modulating the length of the hydrophobic tail of the synthesized calix-[4]-arene compounds. The method of the invention enables the extraction and the separation of soluble and insoluble fractions of a wide range of membrane proteins, depending on the substituents inserted in the calix-[4]-arene-based platform.

According to the invention, the membrane protein can be selected from the group comprising the transport proteins, ion channels, G protein-coupled receptors (GPCRs), enzymes or glycoproteins. In the sense of the present invention, "transport protein", is understood to mean a membrane protein whose role is the transport of various substances (ions, sterols, macromolecules, etc.) on both sides of the membrane.

The step of contacting membrane pellets containing one or more membrane proteins to be extracted with an aqueous solution containing at least one calixarene of formula (I) can be carried out at a pH ranging from 5.5 to 10, preferably from 6 to 9.

The extraction method can be carried out at a temperature ranging from 0 to 100° C., preferably from 4 to 25° C.

The extraction and stabilization methods utilize a concentration of calixarene of formula (I) ranging from 10-6 to 10-2 M.

The method of the extraction according to the invention can be carried out with calixarenes in solution or calixarenes in colloidal aggregates on account of their surface-active property.

In the sense of the present invention, colloidal aggregate is understood to mean groups of a few to a few hundred molecules of calixarene organizing themselves on the basis of forces of repulsion towards the solvent. Given their nature, the calixarenes of formula (I) are capable of forming aggregates in an appropriate medium such as for example in water, in an aqueous solution, in an isotonic medium or in a biological medium.

The aggregate can be selected from the group comprising micelles, liposomes and lipid nanoparticles. Preferably, the calixarenes are in the form of micelles.

The term micelle designates a spheroidal aggregate of molecules of calixarene of formula (I) which organizes itself depending on the solvent used. For example, in water or an aqueous solvent, the lipophilic ends are turned towards the interior of the micelle whereas the hydrophilic ends form the interface of the micelle with the solvent. In an organic solvent, for example oil, the arrangement is reversed. The term liposome designates small artificially made vesicles in particular constituted of thin sheets of phospholipids, separated from one another by aqueous compartments. They can have a structure very close to that of biological membranes.

In the context of the present invention, the term nanoparticle signifies an assembly of a few hundred to a few thousand molecules of calixarene of formula (I), resulting in an object at least one of whose dimensions is of nanometer size, for example between 1 and 300 nm.

The membrane proteins complexed with the calixarenes of formula (I) and the non-complexed membrane proteins can be separated by centrifugation, for example for 2 hours at 4° C. and at a speed of 100 000 g. The centrifugation conditions will depend on the nature of the protein. Those skilled in the art will know how to select the optimal centrifugation conditions.

It will be understood that within the scope of the present invention, various modifications may be made to the embodiments disclosed herein. For example, it must be ensured that the calixarene compounds have a relatively good solubility and considered acceptable for use in the extraction, solubilization and stabilization of membrane proteins.

Therefore, the above description should not be construed as limiting, but merely as exemplifications of preferred embodiments. For example, to modulate the solubility and the physical-chemical properties of calixarene compounds, those skilled in the art will have the capacity to modify the nature of the saccharide units (i.e. monosaccharide, e.g. galactose disaccharide, e.g. maltose) and the multiplicity of the polar heads and/or the length of the hydrophobic aliphatic chain. Those skilled in the art will envision other modifications within the scope and spirit of the claims appended thereto.

3. Examples

The invention is illustrated by two examples of calixarene compound which however do not limit the invention. Example 1 relates to the preparation of the specific CALX173GALO compound with an heptyl chain which belongs to the serie CALX1N3GALO, and example 2 relates to the preparation of CALX173GLUK compound with an heptyl chain which belongs to the serie CALX1N3GLUK.

3.1 Example 1 (CALX173GALO)

The following multi-step synthesis is accorded to reaction scheme 1 and 2.

a) Synthesis of 5,11,17,23-Tetra-tert-butyl-25,26,27, 28-tetrahydroxycalix-[4]-arene (7)

The synthesis of compound 7 is performed as described in reference of Gutsche C D et al., "*Calixarenes. 4. The synthesis, characterization, and properties of the calix-arenes from p-tert-butylphenol*", J. Am. Chem. Soc., 1981, 103, 3782-3792, and the following modifications: In a 5 L erlenmeyer flask are heated at 240° C. a mixture of 4-tert-butylphenol (500 g, 3.33 mol), aqueous solution of formaldehyde at 35% w/v (300 mL, 3.78 mol) and NaOH pellets (2.4 g, 60 mmol) until the formation of a yellow foam. The mixture is cooled then recovered and the solid is grinded with a mortar to obtain a fine yellow powder of linear precursor (540 g). In two necked round bottom flask of 2 L are added 200 g of linear precursor and 1 L of diphenyl ether. A Dean-Stark mounting is adapted and an air flow is sent with a pump then the mixture is heated at refluxed temperature during 3 hours. Then, the reaction mixture is cooled at room temperature. The dark brown suspension is poured in 1 L of ethyl acetate and is let stand overnight. The suspension is filtered, rinsed twice with AcOEt then twice with methanol. The solid is dried in the open air then by vacuum under reduce pressure. 120 g of an off-white solid is obtained as inclusion complex with a molecule of AcOEt in a yield of 52%.

$^1$H NMR (500 MHz, CDCl$_3$); δ (ppm): 1.2 (s, 12H, tBu), 1.26 (t, 3H, J=10 Hz, —CH$_3$AcOEt), 2.04 (s, 3H, CH$_3$CO—AcOEt), 3.5 (d, 4H, J=15 Hz, —CH$_2$— bridges), 4.12 (q, 2H, J=5 Hz, —CH$_2$CO—AcOEt), 4.26 (d, 4H, J=15 Hz, —CH$_2$— bridges), 7.05 (s, 8H, CH$_{Ar}$), 10.34 (s, 4H, ArOH).

$^{13}$C NMR (500 MHz, CDCl$_3$); δ (ppm): 31.4 and 32.7 (—CH$_2$— bridges), 34.8 (tBu), 125.8, 127.7, 144.4, 146.6 (CH$_{Ar}$).

Electrospray ionization (ESI) mass spectrum for C$_{44}$H$_{56}$O$_4$(CHCl$_3$/MeOH 1:1, HCOOH 1%); Calculated: 648.4. Found: m/z=671.5 [M+Na]$^+$ and 693.6 [M+2Na—H]$^+$.

b) Synthesis of 25,26,27,28-Tetrahydroxycalix-[4]-arene (8)

The synthesis of compound 8 is performed as described in reference of Gutsche, C. D. & Levine, J. A.: "*Calixarenes. 6. Synthesis of a functionalizable calix-[4]-arene in a conformational rigid cone conformation*", J. Am. Chem. Soc., 1982, 104, 2652-2653, and the following modifications: In a 6 L reactor is added 3 L of toluene and 200 g of 5,11,17,23-Tetra-tert-butyl-25,26,27,28-tetrahydroxycalix-[4]-arene 7 (0.27 mol) in inclusion complex with AcOEt. The mixture is agitated with a mechanical stirrer and the system is purged with nitrogen during 15 minutes. Once the product is dissolved, 30.6 g of phenol (0.34 mol) and 162.8 g of AlCl$_3$ (1.22 mol) are added in this order. The solution is turned quickly orange and a red viscous material is formed in the reactor walls. The reaction mixture is stirred vigorously during 3 hours. Then, 2.5 L of distilled water is added to neutralize the excess of AlCl$_3$. The organic phase is separated and concentrated at rotary evaporator to obtain an orange heterogeneous solution. Then, 1 L of methanol is added and sonicated for 1 hour the solution in an ultrasonic bath. The suspension is filtered; the solid is washed with MeOH (2×200 mL) and ether (200 mL). Then, the solid is dried in the open air then by vacuum under reduce pressure to recover 105 g of a cream powder with a yield of 95%.

$^1$H NMR (500 MHz, CDCl$_3$); δ (ppm): 3.55 (broad s, 4H, —CH$_2$— bridges), 4.26 (broad s, 4H, —CH$_2$— bridges), 6.73 (t, 4H, J=9 Hz, CH$_{Ar}$), 7.06 (d, 8H, J=9 Hz, CH$_{Ar}$), 10.2 (s, 4H, ArOH).

$^{13}$C NMR (500 MHz, CDCl$_3$); δ (ppm): 31.8 (—CH$_2$— bridges), 122.3, 128.3, 128.8, 148.9 (CH$_{Ar}$).

ESI mass spectrum for C$_{28}$H$_{24}$O$_4$(CHCl$_3$/MeOH 1:1, HCOOH 1%); Calculated: 424.2. Found: m/z=447.0 [M+Na]$^+$.

c) Synthesis of 5,11,17-tris-[(cyano)methyl]-25-heptyloxy-26,27,28-trishydroxycalix-[4]-arene (11)

The synthesis of compound 11 is performed as described in reference of Suwinska, K. et al., "*Trianionic calix[4] arene monoalkoxy derivatives: synthesis, solid-state structures and self-assembly properties*", New J. Chem., 2008, 32, 1988-1998, and the following modifications: In a 250 mL two-necked flask, 30 g of 25,26,27,28-Tetrahydroxy-calix-[4]-arene 8 (70.7 mmol) are dissolved with 100 mL of Dimethylformamide (DMF). The system is purged with argon and the solution is heated at 40° C. After 15 minutes, 6.3 g of NaHCO$_3$ (74.24 mmol) are added in the solution. The solution is stirred vigorously the under a stream of argon. After 15 minutes, at once 17 mL (106 mmol) of iodoheptane are added. Then, the reaction mixture is heated at 40° C. without argon flow. After 5 days, the green solution is cooled at room temperature and poured into 1 L of water. The cloudy aqueous phase is extracted with $CH_2Cl_2$ (3×200 mL). The organic phases are collected and washed with water (2×200 mL) then 200 mL of brine. The organic phase is dried over $MgSO_4$ solution, and then the suspension is filtered and concentrated on a rotary evaporator. A yellow paste residue is obtained after drying under reduce vacuum. A flash chromatography is performed with a quantity of silica twenty times higher than that residue recovered and an elution gradient from pure cyclohexane to $CH_2Cl_2$/Cyclohexane (4:6) to obtain 35 g of a white powder containing a mixture of 5% w/w of unreacted 25,26,27,28-Tetrahydroxycalix-[4]-arene, 80% w/w of 25-heptyloxy-26,27,28-trishydroxycalix-[4]-arene and 15% w/w of 25,27-bisheptyloxy-26,28-bishydroxycalix-[4]-arene. The weight proportions of the isolated mixture are defined by a $^1H$ NMR experiment help to the integrations of singlets located on the spectrum at 10.3, 9.9 and 8.3 ppm corresponding respectively to the cone conformations of 25,26,27,28-Tetrahydroxycalix-[4]-arene, 25-heptyloxy-26,27,28-trishydroxycalix-[4]-arene and 5,27-bisheptyloxy-26,28-bishydroxycalix-[4]-arene. The weight proportions are also calculated by considering the integrations of singlets at 9 and 8.1 ppm corresponding respectively to the 1,2-alternate and 1,3-alternate conformations of 5,27-bisheptyloxy-26,28-bishydroxycalix-[4]-arene.

In a 2 L two-necked flask, the mixture is added, purified and dissolved in 700 mL of THF. The system is purged with argon and 115 mL of glacial acetic acid (1.99 mol), 75 mL of dimethylamine aqueous solution at 40% w/w (0.6 mol) and 56 mL of a formaldehyde aqueous solution at 35% w/w (0.6 mol) are added in this order. Continue bubbling argon into the reaction mixture for 1 hour and further stirring at room without argon flow. After 5 days, the reaction mixture is concentrated on a rotary evaporator and 1 L of an aqueous solution of $Na_2CO_3$ at 10% w/v is added drop wise to the heterogeneous white residue obtained. Once the addition is completed, 500 mL of water is added to the white gel formed, then is extracted with $CH_2Cl_2$ (3×500 mL). The organic phases are collected, dried over $MgSO_4$, filtered and the clear solution is concentrated on a rotary evaporator to give 44 g of a fine white powder after drying under reduce pressure.

In a 1 L two-necked flask is introduced the white powder residue containing predominantly the 5,11,17-tris-[(dimethylamino)methyl]-25-heptyloxy-26,27,28-trishydroxycalix-[4]-arene, then 430 mL of DMSO are added. The heterogeneous solution is purged with argon, and heated at 40° C. Then, 10 mL of iodomethane (161 mmol) are added dropwise slowly over a period of 5 minutes and the solution is stirred 1 hour at 40° C. After the solubilization is completed, 15.8 g (322 mmol) of sodium cyanide are added to the yellow solution. Then, the reaction mixture is heated under argon flow at 80° C. After 48 hours, the reaction mixture is cooled at room temperature and pours the reaction mixture is poured in a 5 L erlenmeyer flask containing 2 L of iced water and 400 mL of an aqueous HCl 1N solution to neutralize excess of sodium cyanide. The white suspension is extracted with $CH_2Cl_2$ (3×500 mL). The organic phases are collected, washed with water (2×500 mL) then brine (500 mL), then are dried over $MgSO_4$, filtered and concentrated on a rotary evaporator to give 33 g of a brown solid residue. The solid residue is purified with a flash chromatography on silica gel with an elution gradient of AcOEt/Cyclohexane from 3:7 to 1:1 to recover 21.4 g of a yellow powder with a yield of 47%.

$^1H$ NMR (500 MHz, CDCl3); δ (ppm): 0.97 (t, 3H, J=6.2 Hz, —CH3), 1.45-1.76 (m, 8H, —CH2-heptyl chain), 2.19-2.26 (m, 2H, —CH2-CH3), 3.5 (dd, 4H, J=6.2 Hz and J=13.8 Hz, —CH2-bridges), 3.59 (s, 2H, —CH2CN), 3.6 (s, 4H, —CH2CN), 4.2 (t, 2H, J=7 Hz, OCH2-), 4.28-4.44 (dd, 4H, J=13.2 Hz and J=18.6 Hz, —CH2-bridges), 6.93-7.3 (m, 9H, CHAr), 9.5 (s, 2H, ArOH), 9.75 (s, 1H, ArOH).

$^{13}C$ NMR (CDCl3); δ (ppm): 14.1 (—CH3), 22.6 (—CH2-CN), 22.8, 25.8, 29.1, 29.9 (—CH2-alkyl chain), 31.4, 32.0 (—CH2-bridges), 77.5 (ArOCH2-), 118.3 (—C≡N), 122.1, 123.2 (CAr—CH2-CN), 126.4, 128.3, 128.5, 128.7, 129.4, 129.5, 133.9 (CHAr), 149.2, 150.6 (CAr—OH), 151.5 ($\underline{C}_{Ar}$—OCH$_2$—).

ESI mass spectrum for $C_{41}H_{41}N_3O_4$ (CHCl3/MeOH 1:1, HCOOH 1%); Calculated: 424.2. Found: m/z=662.1 [M+Na]$^+$.

d) Synthesis of 5,11,17-tris-[(carboxylato)methyl]-25-heptyloxy-26,27,28-trishydroxycalix-[4]-arene (12)

The synthesis of compound 12 is performed as described in reference of Suwinska, K. et al., "Trianionic calix[4]arene monoalkoxy derivatives: synthesis, solid-state structures and self-assembly properties", New J. Chem., 2008, 32, 1988-1998, and the following modifications: In a 500 mL PFA flask are introduced 21.4 g of 5,11,17-tris-[(cyano) methyl]-25-heptyloxy-26,27,28-trishydroxycalix-[4]-arene 11 (33.45 mmol), and are solubilized with 300 mL of mixture EtOH/THF (5:1); then 120 mL of an aqueous KOH 3M solution are added. The reaction mixture is heated at reflux with vigorous stirring. After 48 hours, the reaction mixture is cooled at room temperature and the solution is poured in a 2 L erlenmeyer flask containing 800 mL of an iced aqueous HCl 1N solution. The yellow suspension is extracted with CH2Cl2 (3×200 mL). The organic phases are collected, dried over MgSO4, filtered and concentrated on a rotary evaporator to recover 24.4 g of a yellow powder. The residue is purified by flash chromatography on silica gel with an elution gradient with AcOH/MeOH/CH2Cl2 from 1:2:97 to 1:6:93 to yield 20.4 g of a cream powder after drying under reduce pressure. The residue is solubilized with 1 L of ether and is washed with water (10×200 mL) to remove the acid acetic traces. The organic phase is dried over MgSO4, is filtered and concentrated on a rotary evaporator. The residue is dried overnight in a desiccator under reduce pressure to recover 17.9 g of a white powder in a yield of 77%.

$^1H$ NMR (500 MHz, CDCl3); δ (ppm): 0.97 (t, 3H, J=6.2 Hz, —CH3), 1.43-1.69 (m, 8H, —CH2-heptyl chain), 2.18 (m, 2H, —CH2-CH3), 3.42 (m, 10H, —CH2-bridges and —CH2CO2H), 4.16-4.37 (m, 6H, OCH2- and —CH2-bridges), 6.89-7.1 (m, 9H, CHAr), 9.44 (s, 2H, ArOH), 9.69 (s, 1H, ArOH).

$^{13}C$ NMR (CDCl3); δ (ppm): 14.1 (—CH3), 22.7, 25.9, 29.4, 29.9 (—CH2-alkyl chain), 31.5, 32.0 (—CH2-bridges), 40.2 (—CH2-CO2H), 76.7 (ArOCH2-), 125.4, 126.2 (CAr—CH2-CO2H), 126.5, 128.4, 128.5, 128.8, 129.5, 129.7, 134.0 (CHAr), 148.5, 150.1 (CAr—OH), 151.5 (CAr—OCH2-), 177.9 (—CO2H).

ESI mass spectrum for C41H44O10 (CHCl3/MeOH 1:1, HCOOH 1%); Calculated: 696.3. Found: m/z=719.2 [M+Na]+, 741.2 [M+2Na—H]+, 763.1 [M+3Na—2H]+ and 785.0 [M+4Na-3H]+.

e) Synthesis of methyl 25-heptyloxy-26,27,28-tris-methoxycalix-[4]-arene-5,11,17-trisacetate ester (13)

In a 100 mL two-necked round bottom flask are introduced 5 g of 5,11,17-tris-[(carboxylato)methyl]-25-heptyloxy-26,27,28-trishydroxycalix-[4]-arene 12 (7.18 mmol), then are dissolved with 50 ml of DMF. The system is purged by bubbling nitrogen through the reaction mixture and small portions 2.07 g of sodium hydride at 60% w/w in mineral oil (51.7 mmol) are added over a period of 5 minutes. Then, 9.8 mL of iodomethane (157.4 mmol) are added to the yellow solution over a period of 10 minutes and the reaction mixture is stirred at room temperature under a nitrogen flow. The reaction progress is monitored by TLC with eluent AcOEt/Cyclohexane (3:7). After 16 hours of reaction, the reaction mixture is poured in 500 mL of water and the aqueous phase is extracted with $CH_2Cl_2$ (3×200 mL). The organic phases are collected and washed with water (2×200 mL) then 200 mL of brine. The organic phase is dried over $MgSO_4$, filtered and concentrated on a rotary evaporator to recover 15.5 g of a yellow liquid. The residue is purified by flash chromatography on silica gel with an eluent AcOEt/Cyclohexane (2:8) to give 3.85 g of a yellow powder with a yield of 75%.

$^1$H NMR (500 MHz, $CDCl_3$); ((ppm): 0.91 (t, 3H, J=6.63 Hz, —C$\underline{H}_3$), 1.25-1.56 (m, 8H, —C$\underline{H}_2$— heptyl chain), 1.86-1.91 (m, 2H, —$CH_2$—$CH_3$), 3.0 (s, 2H, —C$\underline{H}_2$—$CO_2Me$), 3.04-3.34 (m, 5H, —C$\underline{H}_2$— bridges), 3.54-3.73 (m, 22H, 2× —C$\underline{H}_2$—$CO_2Me$, 3× —$CO_2C\underline{H}_3$, ArO—C$\underline{H}_2$—, —C$\underline{H}_2$— bridges, 2× 2× ArO—C$\underline{H}_3$), 3.87 (s, 3H, ArO—C$\underline{H}_3$), 4.04 (t, J=15 Hz, 1H), 4.32 (t, J=15 Hz, 1H, —C$\underline{H}_2$— bridges), 6.05-6.53 (m, 3H, C$\underline{H}_{Ar}$ calixarene), 6.75-7.33 (m, 6H, C$\underline{H}_{Ar}$ calixarene).

$^{13}$C NMR ($CDCl_3$); δ (ppm): 14.1 (—$\underline{C}H_3$), 22.7, 26.4, 29.2, 29.3 (—$\underline{C}H_2$— alkyl chain), 30.5 (—$\underline{C}H_2$— bridges), 30.7, 31.9 (—$\underline{C}H_2$— alkyl chain), 35.9, 40.6 (—$\underline{C}H_2$—$CO_2Me$), 40.8 (—$\underline{C}H_2$— bridges), 51.8, 52.0 (—$\underline{C}O_2CH_3$), 59.5, 60.7 (ArO—$\underline{C}H_3$), d 74.2, 75.2 (ArO—$\underline{C}H_2$—), 121.5, 126.4 ($\underline{C}_{Ar}$—$CH_2$—), 127.2-137.0 ($\underline{C}H_{Ar}$), 156.0-157.9 ($\sqrt{\underline{C}}_{Ar}$—OMe, $\underline{C}_{Ar}$—$OCH_2$—), 172.5, 172.6 (—$\underline{C}O_2Me$).

ESI mass spectrum for $C_{47}H_{56}O_{10}$ ($CHCl_3$/MeOH 1:1, HCOOH 1%); Calculated: 780.4. Found: m/z=781.4 $[M+H]^+$, 803.3 $[M+Na]^+$ and 819.4 $[M+K]^+$.

f) Synthesis of 5,11,17-tris-(2-hydroxyethyl)-25-heptyloxy-26,27,28-trishydroxycalix-[4]-arene (3)

In a 250 mL two-necked round bottom flask are introduced 3.85 g of 25-heptyloxy-26,27,28-trishydroxycalix-[4]-arene-5,11,17-tris-(ethylacetate) ester 13 (4.93 mmol), then are dissolved with 150 mL of THF. The system is purged by bubbling nitrogen through the reaction mixture, and small portions 681 mg of $LiAlH_4$ (17.94 mmol) are added. The resulting suspension is stirred at room temperature under a nitrogen flow. The reaction progress is monitored by TLC with eluent AcOEt/Cyclohexane (3:7). After 2 hours of reaction, the reaction mixture is poured in 200 mL of an iced 1N HCl solution, and the suspension is extracted with $CH_2Cl_2$ (3×150 mL). The organic phases are collected, dried over $MgSO_4$, filtered and concentrated on a rotary evaporator to recover 4 g of a white powder after drying under reduce pressure. The residue is purified by flash chromatography on silica gel with an elution gradient with AcOEt/Cyclohexane from 6:4 to 7:3 to give 2.63 g of a white powder with a yield of 76%.

$^1$H NMR (500 MHz, $CDCl_3$); δ (ppm): 0.91 (t, J=6.2 Hz, 3H), 1.25-1.62 (m, 8H, —C$\underline{H}_2$— heptyl chain), 1.71-2.04 (m, 5H, ArOC$\underline{H}_2$—C$\underline{H}_2$—, 3× —$CH_2$—O$\underline{H}$), 2.36 (t, J=15 Hz, 1H, —C$\underline{H}_2$— bridges), 2.52 (t, J=15 Hz, 1H, —C$\underline{H}_2$— bridges), 2.68 (s br, 1H, —C$\underline{H}_2$— bridges), 2.8-2.87 (m, 3H, —C$\underline{H}_2$— bridges, —C$\underline{H}_2$—OH), 3.01-3.19 (m, 6H, 2× —C$\underline{H}_2$—OH, —C$\underline{H}_2$— bridges), 3.44-3.95 (m, 17H, 3× ArC$\underline{H}_2$—, 3× ArO—C$\underline{H}_3$, ArO—$CH_2$—), 3.99-4.08 (m, 1H, —C$\underline{H}_2$— bridges), 4.35 (d, J=13.8 Hz, 1H, —C$\underline{H}_2$— bridges), 6.17 (d, 1H, J=5 Hz, C$\underline{H}_{Ar}$ calixarene), 6.36-6.58 (m, 2H, C$\underline{H}_{Ar}$ calixarene), 6.77-7.19 (m, 6H, C$\underline{H}_{Ar}$ calixarene).

$^{13}$C NMR ($CDCl_3$); δ (ppm): 14.1 (—$\underline{C}H_3$), 22.6, 26.3, 29.3 (—$\underline{C}H_2$— alkyl chain), 30.2, 30.6, 30.8 (—$\underline{C}H_2$— bridges), 31.9 (—$\underline{C}H_2$— alkyl chain), 36.2, 36.5 (Ar—$\underline{C}H_2$—), 38.1, 38.4, 38.7 (—$\underline{C}H_2$— bridges), 59.0, 59.7, 61.2 (ArO—$\underline{C}H_3$), 63.4, 63.6, 63.9 (—$\underline{C}H_2$—OH), 73.2, 74.5 (ArO—$\underline{C}H_2$—), 122.3 ($\underline{C}_{Ar}$—$CH_2$—), 127.0-136.8 ($\underline{C}H_{Ar}$), 155.7-156.8 ($\underline{C}_{Ar}$—OMe, $\underline{C}_{Ar}$—$OCH_2$—).

ESI mass spectrum for $C_{44}H_{56}O_7$($CHCl_3$/MeOH 1:1, HCOOH 1%); calculated: 696.4. Found: m/z=697.4 $[M+H]^+$ and 719.2 $[M+Na]^+$.

g) Synthesis of 5,11,17-Tris[2-(b-D-galactopyranosyloxy)ethyl]-25-heptoxy-26,27,28-trismethoxy-calix[4]arene (CALX173GALO=5)

The synthesis of compound CALX173GALO is performed via a glycosylation procedure described in reference "Dondoni, A. et al, *Synthesis and Properties of O-Glycosyl Calix[4]Arenes (Calixsugars)*", Chem. Eur. J., 1997, 3, 1774-1782, and the following modifications: In a 100 mL round bottom flask, 372 mg of 5,11,17-Tris-(2-hydroxyethyl)-25-heptyloxy-26,27,28-trishydroxycalix-[4]-arene 3 are introduced (0.534 mmol) and azeotroped from toluene (3×10 mL) on a rotary evaporator. In the same manner, 2.05 g of 2,3,4,6-tetra-O-benzoyl-1-thio-b-D-galactopyranoside 2 (3.3 mmol) are weighted in another flask and azeotroped from toluene (3×20 mL) on a rotary evaporator. The residue powders are dried on a desiccator overnight. The quantity of dried compound 2 is divided into three equal fractions (about 685 mg, 1.1 mmol). In a 25 mL two-necked round bottom flask are introduced the dried compound 3 and the system is purged with argon. The dried compound 3 is dissolved with 8 mL of freshly distilled acetonitrile and, activated 3A molecular sieves are added while argon is bubbling through the suspension. The reaction mixture is stirred for 15 minutes under an argon stream then one fraction of compound 2 is added. The heterogeneous medium is sonicated 1 minute in an ultrasonic bath with the flow of argon. After 15 minutes, 401 mg of copper (II) triflate (1.1 mmol) and molecular sieve 3A are added. The green heterogeneous medium is sonicated 1 minute in an ultrasonic bath and the flow of argon is continued. Every 15 minutes, successively 1.1 mmol of 2, 1.1 mmol of copper (II) triflate and molecular sieve 3A are added, and the reaction mixture is sonicated 1 minute with an ultrasonic bath. This operation is repeated two times and the reaction is continued at room temperature under a flow of argon. After 30 minutes, the reaction is completed according to the TLC monitoring with eluent AcOEt/Cyclohexane (3:7). Then, 10 mL of TEA are added to the reaction mixture, then the dark brown suspension is filtered through celite, and washed several times with AcOEt, and concentrated on a rotary evaporator, then dried under reduced vacuum to recover 6.28 g of a brown residue. The residue is dissolved with a minimum quantity of AcOEt and is passed through a layer of silica gel (d×h, 10×5 cm$^2$) and eluted with AcOEt (3×150 mL). The filtrate is concentrated on a rotary evaporator to give 3.42 g of a yellow powder residue. The residue is purified by flash chromatography on silica gel with a gradient elution of AcOEt/Cyclohexane from 25:75 to 3:7 and yield 729 mg of a yellow powder. The residue is purified by size exclusion chromatography on Sephadex LH-20 with a mixture of MeOH/CH$_2$Cl$_2$ (1:1) to give 341 mg of a yellow powder. The powder is dissolved in 10 ml of a mixture of distilled solvents MeOH/CH$_2$Cl$_2$ (1:1). The reaction mixture is purged with argon, and a catalytic amount of sodium methoxide is added to obtain a pH of 10-12 in the reaction mixture. The reaction is monitored by TLC with an eluent AcOEt/iPrOH/H$_2$O (5:3:2). After 20 h, the medium is neutralized with Amberlite IR-120 (H+), and then the pink solution is filtered and concentrated on a rotary evaporator. The residue is purified by size exclusion chromatography on Sephadex LH-20 with a mixture of MeOH/CH$_2$Cl$_2$ (1:1). The purified residue is dissolved in 5 mL of MilliQ® water and the freezed sample is lyophilized. After 4 days of lyophilisation, 123 mg of a light brown powder are recovered (0.104 mmol) with a yield of 20%.

Matrix-assisted laser desorption-ionization/Time-of-flight mass spectrometry (MALDI/TOF) mass spectrum for C$_{62}$H$_{86}$O$_{22}$ (matrix DTCB+NaI): Calculated: 1182.6. Found: m/z=1206.7 [M+Na]$^+$.

3.2 Example 2 (CALX173GLUK)

The following multi-step synthesis is accorded to reaction scheme 3.

a) Synthesis of 5,11,17-tris-(2-azidoethyl)-25-heptyloxy-26,27,28-trishydroxycalix-[4]-arene (16)

The synthesis of compound 16 is performed as the Mitsunobu procedure described in the publication of Dondoni, A. & Marra, A: "*C-Glycoside Clustering on Calix[4]arene, Adamantane, and Benzene Scaffolds through 1,2,3-Triazole Linkers*", The Journal of Organic Chemistry, 2006, 71, 7546-7557, and the following modifications: In a two-necked 50 mL round bottom flask are introduced 3.1 g of 5,11,17-tris-(2-hydroxyethyl)-25-heptyloxy-26,27,28-trishydroxycalix-[4]-arene 3 (4.45 mmol) and are dissolved with 20 mL of DMF. The system is purged by bubbling nitrogen through the reaction mixture, then 1.78 g of sodium azide (27.4 mmol), 6 mL of diphenyl phosphoryl azide (26.5 mmol) and 2 mL of 1,8-Diazabicyclo-[5.4.0]-undec-7-ene (13.4 mmol) are added. The reaction mixture is stirred vigorously at 120° C. under a nitrogen flow during 22 hours. The reaction progress is monitored by TLC with eluent AcOEt/Cyclohexane (7:3). The brown reaction is cooled at room temperature, and then the mixture poured in 200 mL of iced water. The reaction mixture is extracted with CH$_2$Cl$_2$ (3×100 mL). The organic phases are collected, washed with H$_2$O (2×100 mL) and brine (100 mL), dried over MgSO$_4$, filtered and concentrated on a rotary evaporator to recover a brown liquid after drying under reduce pressure. The residue is purified by flash chromatography on silica gel with an eluent AcOEt/Cyclohexane 5:95 to give 2.73 g of a colourless oil with a yield of 80%.

$^1$H NMR (500 MHz, CDCl$_3$); δ (ppm): 0.92 (t, J=6.4 Hz, 3H, —C$\underline{H}_3$), 1.12-1.72 (m, 8H, —C$\underline{H}_2$— heptyl chain), 1.87-1.90 (m, 2H, ArOCH$_2$—C$\underline{H}_2$—), 2.29 (t, J=10 Hz, 1H, —C$\underline{H}_2$— bridges), 2.42-2.61 (m, 1H, —C$\underline{H}_2$— bridges), 2.79 (t, J=10 Hz, 1H, —C$\underline{H}_2$— bridges), 2.83-3.21 (m, 9H, 3× —C$\underline{H}_2$—N$_3$, —C$\underline{H}_2$— bridges), 3.46-3.94 (m, 17H, 3× ArO—C$\underline{H}_3$, ArO—C$\underline{H}_2$—, 3× Ar—C$\underline{H}_2$—), 4.05 (d, J=10 Hz, 1H, —C$\underline{H}_2$— bridges), 4.28-4.4 (m, 1H, —C$\underline{H}_2$— bridges), 6.02-6.56 (m, 3H, C$\underline{H}_{Ar}$ calixarene), 6.72-7.18 (m, 6H, C$\underline{H}_{Ar}$ calixarene).

$^{13}$C NMR (CDCl$_3$); δ (ppm): 14.1 (—C$\underline{H}_3$), 22.6, 26.3, 29.3 (—C$\underline{H}_2$— alkyl chain), 30.5, 30.6, 30.8 (—C$\underline{H}_2$— bridges), 31.9 (—C$\underline{H}_2$— alkyl chain), 34.2, 34.4, 34.7 (—C$\underline{H}_2$— bridges), 35.8, 36.0 (Ar—C$\underline{H}_2$—), 52.8, 52.9, 53.0 (—C$\underline{H}_2$—N$_3$), 58.9, 59.6 (—C$\underline{H}_2$— bridges), 60.8, 61.0, 62.4 (ArO—C$\underline{H}_3$), 74.2, 75.3 (ArO—C$\underline{H}_2$—), 121.6, 121.9 (C$_{Ar}$—CH$_2$—), 127.2-137.0 (C$\underline{H}_{Ar}$), 155.9-157.7 (C$_{Ar}$—OMe, C$_{Ar}$—OCH$_2$—).

ESI mass spectrum for C$_{44}$H$_{53}$N$_9$O$_4$ (CHCl$_3$/MeOH 1:1, HCOOH 1%); Calculated: 771.4. Found: m/z=794.5 [M+Na]$^+$.

b) Synthesis of 5,11,17-Tris{2-[4-(b-D-glucopyranosyl)-1H-1,2,3-triazol-1-yl]-ethyl}-25-heptoxy-26,27,28-trismethoxy-calix[4]arene (CAL173GLUK=18)

The synthesis of compound CALX173GLUK is performed as the CuAAC procedure described in the publication of Dondoni, A. & Marra, A: "*C-Glycoside Clustering on Calix[4]arene, Adamantane, and Benzene Scaffolds through 1,2,3-Triazole Linkers*", The Journal of Organic Chemistry, 2006, 71, 7546-7557, and the following modifications: In a 100 mL round bottom flask are introduced 2.73 g of 5,11,17-tris-(2-azidoethyl)-25-heptyloxy-26,27,28-trishydroxycalix-[4]-arene 16 (3.54 mmol) and are dissolved with 50 mL of anhydrous DMF. The system is purged by bubbling nitrogen through the reaction mixture and activated 4 A molecular sieves are added. Then, the suspension is stirred 5 minutes under an argon flow, then 6.13 g of propargyl 2,3,4,6-tetra-O-acetyl-β-D-glucopyranose 15 (15.87 mmol), 4.8 mL of distilled DIEA (27.56 mmol) and 498 mg of CuI (2.61 mmol) are added in this order. The reaction mixture is sonicated during one minute. The reaction mixture is protected from the light and is stirred at room temperature under an argon flow. The reaction progress is monitored by TLC with the eluant AcOEt/Cyclohexane (5:95). After 24 h, the orange suspension is filtered through Celite and is washed with AcOEt (3×100 mL). The filtrate is washed with distilled water (500 mL), a solution of 1M sodium phosphate pH 7 (2×100 mL) and brine (100 mL). The organic phase is dried over MgSO$_4$, is filtered and concentrated on a rotary evaporator to recover 9.27 g of a brown powder after drying under reduce pressure. The residue is purified by flash chromatography on silica gel with a gradient elution of AcOEt/Cyclohexane from 95:5 to pure AcOEt and 6.76 g of a yellow powder is obtained. The residue is purified by size exclusion chromatography on Sephadex LH-20 with a mixture of MeOH/CH$_2$Cl$_2$ (1:1) to give 5.35 g of a light brown powder. The residue is dissolved in 50 mL of freshly distilled MeOH. The reaction mixture is purged with argon, and a catalytic amount of sodium methoxide is added to obtain a pH of 10-12 in the reaction mixture. The reaction is monitored by TLC with an eluant AcOEt/MeOH/H$_2$O (7:2:1). After 16 h, the medium is neutralized with Amberlite IR-120 (H+), the yellow solution is filtered and concentrated on a rotary evaporator to recover 4.73 g of a yellow powder after drying under reduce pressure. The residue is purified by size exclusion chromatography on Sephadex LH-20 with a mixture of MeOH/CH$_2$Cl$_2$ (1:1) to give 4.64 g of a light brown powder. The residue is dissolved in 60 mL of MilliQ® water and the freezed sample is lyophilized. After 4 days of lyophilisation, 3.61 g of a white powder (2.53 mmol) are recovered with a yield of 71%.

MALDI/TOF mass spectrum for $C_{71}H_{95}N_9O_{22}$ (matrix DTCB+NaI); Calculated: 1426.6. Found: m/z=1448.1 $[M+Na]^+$ and $[M+K]$ 1464.7.

Figure 3B:
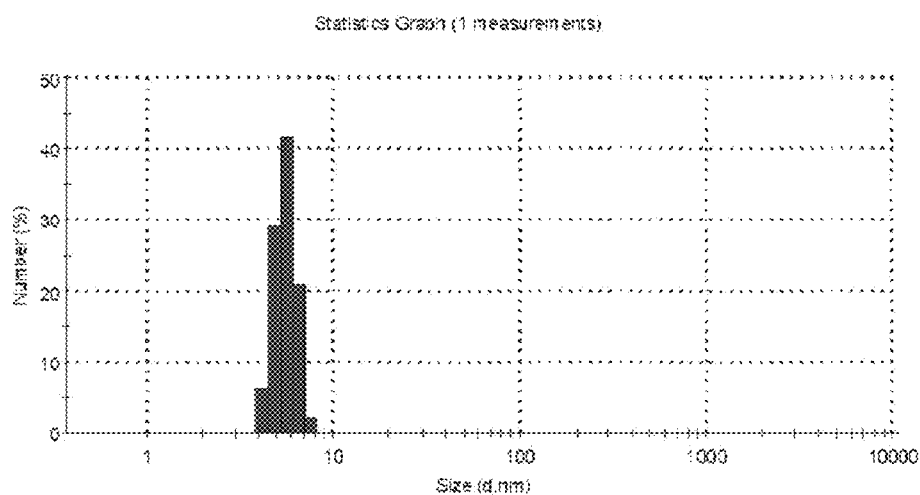

3.3 Properties of CALX173GALO and CALX173GLUK a) Surfactant Properties of CALX173GALO and CALX173GLUK As shown in FIG. 2, CALX173GALO and CAL173GLUK behave like detergents with a Critical Micellar Concentration (CMC) which can range from 0.02 mM to 0.15 mM. Critical Micellar Concentration (CMC) is understood to mean the concentration beyond which the concentration of the detergent molecules no longer increases since said molecules are involved in micelles.

b) Size of Aggregates (FIGS. 3a and 3b)

FIGS. 3a and 3b show the aggregation state of CALX173GALO and CALX173GLUK. As illustrated, all the systems observed form aggregates of the micellar type.

$d_{particules}$ (CALX173GALO)=5.46 nm
$d_{particules}$ (CALX173GLUK)=5.53 nm c) Fluorescence Measurements Fluorescence emission spectra of synthesized calixarene compounds containing 20 μM of pyrene were recorded using an excitation wavelength of 335 nm and the intensities I1 and I3 were measured at the wavelengths corresponding to the first and third vibronic bands located near 373 and 384 nm. The ratio I1/I3 is the so-called pyrene 1:3 ratio.

d) Biological Membrane Solubilization Capacity of CALX173GALO and CALX173GLUK

Solubility Test of Protein of Interest: $A_{2A}$ Adenosine.

The protein content was set at 20 mg/ml (20 mM Tris-Cl pH 8.0, 150 mM NaCl, 10% Glycerol). The solubilization is effected at 4° C. The solubilized or non-solubilized protein fractions are separated by a 100 000 g centrifugation step for 1 hour at 4° C.

FIGS. 4a) and 4b) show the test of solubilization of membrane proteins enriched in $A_{2A}$ adenosine protein with CALX173GALO (Western Blot "C") and CALX173GLUK (Western Blot "D" and "E") calixarenes of the present invention, and also known detergents, e.g. n-Dodecyl-β-D-Maltopyranoside (called DDM, Western Blot "A") and 25-heptyloxy-26,27,28-tris(hydroxyl)calix-[4]-arene-5,11, 17-tris(acetic acid) sodium salt (called here "CALX173ACE", Western Blot "B").

The solubility of $A_{2A}$ adenosine protein is partial with DDM, CALX173GALO, and CALX173ACE at 20 CMC and is nonexistent with CALX173GLUK to 8 CMC. It appears that the solubilization of $A_{2A}$ protein is better with CALX173GALO than reference compounds, i.e. DDM and CALX173ACE (about 20%). The use of CALX173GLUK at 20 CMC enhances the solubilization of the $A_{2A}$ protein.

Stability Test of Protein of Interest: Bacteriorhodopsin Protein (bR).

The study of stabilization of bR protein was conducted in time over several months, at room temperature and at 37° C., with seven conditions of stabilization for the bR protein by using different amphiphilic stabilizers which have shown their interest in the literature; FIG. 5 shows the effect of stabilization of membrane protein bR over the time at room temperature then 37° C. in various detergent conditions: Octyl Glucoside (OG), CALX173ACE, CALX173GALO, CALX173GLUK, Amphipol A8-35, FA-3 Facial Amphiphilic, and Maltose-Neopentyl Glycol (MNG). The monitoring of the conformation of the protein by characteristic measurement of the absorbance at 550 nm shows that after 1 month and a half exposure of the protein at 37° C. in the dark (see FIG. 5):

CALX173GLUK maintains the bR protein in solution in a non-aggregated conformational form a with high absorbance of 0.75;

CALX173GALO, A8-35 and MNG-12 stabilizers have an absorbance value around 0.4;

stability of the bR protein is nonexistent by using OG and FA-3 stabilizers.

What is claimed is:

1. A calixarene compound according to a formula:

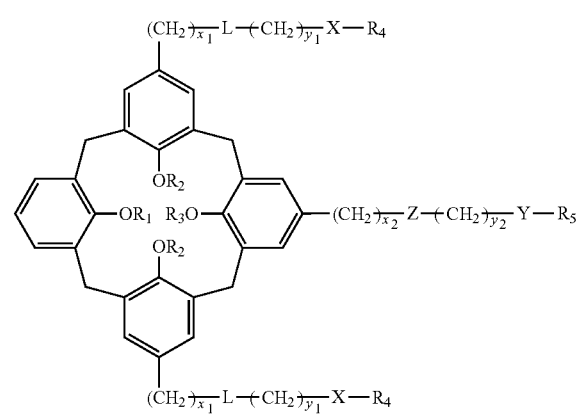

wherein:
$R_1$ represents a linear or branched $C_{(1-16)}$ alkyl group;
$R_2$ represents an hydrogen atom or a methyl group;
$R_3$ is identical to $R_1$ or $R_2$ group;
$R_4$ represents a saccharide residue, in which hydroxyl groups are not protected;
$R_5$ is identical to $R_4$, or is absent;
L is a linker, which is selected from the group consisting of 1,2,3-triazole function, amide function, thiourea function, or is absent;
Z is identical to L or absent;
$0 \leq x_1 \leq 3$, wherein $x_1$ is an integer;
$0 \leq y_1 \leq 3$, wherein $y_1$ is an integer;
$x_2$ is identical to $x_1$ or equal to 0;
$y_2$ is identical to $y_1$ or equal to 0;
X=O, S or is absent; and
Y is identical to X or is absent.

2. The calixarene compound of claim 1, wherein:
$R_1$ represents a linear or branched $C_{(1-16)}$ alkyl group;
$R_2$ represents an hydrogen atom or a methyl group;
$R_3$ is identical to $R_1$ or $R_2$ group;
$R_4$ represents a saccharide residue, in which hydroxyl groups are not protected, which is selected from the group of monosaccharides or disaccharides;
$R_5$ is identical to $R_4$, or is absent;
L is a linker, which is selected from the group consisting of 1,2,3-triazole function, amide function, thiourea function, or is absent;
Z is identical to L, or is absent;
$0 \leq x_1 \leq 3$, wherein $x_1$ is an integer;
$0 \leq y_1 \leq 3$, wherein $y_1$ is an integer;
$x_2$ is identical to $x_1$ or equal to 0;
$y_2$ is identical to $y_1$ or equal to 0;
X=O, S or is absent; and
Y is identical to X or is absent.

3. The calixarene compound of claim 1, wherein:
$R_1$ represents a linear or branched $C_{(1-16)}$ alkyl group;
$R_2$ represents an hydrogen atom or a methyl group;
$R_3$ is identical to $R_1$ or $R_2$ group;
$R_4$ represents a saccharide residue, in which hydroxyl groups are not protected, which is selected from the group consisting of glucosyl, mannosyl, galactosyl, maltosyl, and lactosyl;
$R_5$ is identical to $R_4$, or is absent;
L is a linker, which is selected from the group consisting of 1,2,3-triazole function, amide function, thiourea function, or may be absent;
Z is identical to L, or is absent;
$0 \leq x_1 \leq 3$, wherein $x_1$ is an integer;
$0 \leq y_1 \leq 3$, wherein $y_1$ is an integer;
$x_2$ is identical to $x_1$ or equal to 0;
$y_2$ is identical to $y_1$ or equal to 0;
X=O, S or is absent; and
Y is identical to X or is absent.

4. The calixarene compound of claim 1, wherein:
$R_1$ represents a linear or branched $C_{(1-16)}$ alkyl group;
$R_2$, $R_3$ represent an hydrogen atom or a methyl group;
$R_4$, $R_5$ represent a saccharide residue, in which hydroxyl groups are not protected, which is selected from the group consisting of glucosyl, mannosyl, galactosyl, maltosyl, and lactosyl;
L,Z are a linker, which is selected from the group consisting of 1,2,3-triazole function, amide function, thiourea function, or is absent;
$0 \leq x_{1,2} \leq 3$, wherein $x_{1,2}$ are an integer;
$0 \leq y_{1,2} \leq 3$, wherein $y_{1,2}$ are an integer;
X represents an oxygen atom, a sulfur atom, or is absent; and
Y is identical to X or is absent.

5. The calixarene compound of claim 1, wherein:
$R_1$ corresponds to a linear or branched $C_{(1-16)}$ alkyl group;
$R_2$, $R_3$ are methyl;
$R_4$, $R_5$ represent a saccharide residue, in which hydroxyl groups are not protected, which is selected from the group consisting of glucosyl, mannosyl, galactosyl, maltosyl, and lactosyl;
L is a linker, which is selected from the group consisting of 1,2,3-triazole function, amide function, thiourea function, or is absent;
Z is identical to L or is absent;
$0 \leq x_{1,2} \leq 3$, wherein $x_{1,2}$ are an integer;
$0 \leq y_{1,2} \leq 3$, wherein $y_{1,2}$ are an integer;
X represents an oxygen atom, a sulfur atom, or is absent; and
Y is identical to X or is absent.

6. The calixarene compound of claim 1, wherein:
$R_1$ corresponds to a linear or branched $C_{(1-16)}$ alkyl group;
$R_2$, $R_3$ are methyl;
$R_4$, $R_5$ represent a galactosyl group, in which hydroxyl groups are not protected;
L,Z are absent;
$0 \leq x_{1,2} \leq 3$, wherein $x_{1,2}$ are an integer;
$0 \leq y_{1,2} \leq 3$, wherein $y_{1,2}$ are an integer;
X represents an oxygen atom, a sulfur atom, or is absent; and
Y is identical to X or is absent.

7. The calixarene compound of claim 1, wherein:
$R_1$ corresponds to a linear or branched $C_{(1-16)}$ alkyl group;
$R_2$, $R_3$ are methyl;
$R_4$, $R_5$ represent a glucosyl group, in which hydroxyl groups are not protected;
L,Z are a 1,2,3-triazole function;
$0 \leq x_{1,2} \leq 3$, wherein $x_{1,2}$ are an integer;
$0 \leq y_{1,2} \leq 3$, wherein $y_{1,2}$ are an integer;
X represents an oxygen atom, a sulfur atom, or is absent; and
Y is identical to X or is absent.

8. The calixarene compound of claim 1, wherein:
$R_1$, $R_3$ correspond to a linear or branched $C_{(1-16)}$ alkyl group;
$R_2$ represents an hydrogen atom or a methyl group;
$R_4$ represents a maltosyl group, in which hydroxyl groups are not protected;
$R_5$ is absent;
L is a linker, which is selected from the group consisting of 1,2,3-triazole function, amide function, thiourea function, or is absent;
Z is absent;
$0 \leq x_1 \leq 3$, wherein $x_1$ are an integer;
$0 \leq y_1 \leq 3$, wherein $y_1$ are an integer;
$x_2$ and $y_2$ are equal to 0;
X=O, S or is absent; and
Y is absent.

9. The calixarene compound of claim 1, wherein:
$R_1$, $R_3$ correspond to a linear or branched $C_{(1-16)}$ alkyl group;
$R_2$ represents a methyl;
$R_4$ represents a maltosyl group, in which hydroxyl groups are not protected;
$R_5$ is absent;
L is a linker, which is selected from the group consisting of 1,2,3-triazole function, amide function, thiourea function, or is absent;
Z is absent;
$0 \leq x_1 \leq 3$, wherein $x_1$ are an integer;
$0 \leq y_1 \leq 3$, wherein $y_1$ are an integer;
$x_2$ and $y_2$ are equal to 0;
X=O, S or is absent; and
Y is absent.

10. The calixarene compound of claim 1, wherein:
$R_1$, $R_3$ correspond to a linear or branched $C_{(1-16)}$ alkyl group;
$R_2$ represents a methyl;
$R_4$ represents a maltosyl group, in which hydroxyl groups are not protected;
$R_5$ is absent;
L is a 1,2,3-triazole function;
Z is absent;
$0 \leq x_1 \leq 3$, wherein $x_1$ are an integer;
$0 \leq y_1 \leq 3$, wherein $y_1$ are an integer;
$x_2$ and $y_2$ are equal to 0;
X=O, S or is absent; and
Y is absent.

11. A method for selectively extracting, solubilizing and/or stabilizing membrane proteins, the method comprising:
contacting membrane pellets containing one or more membrane proteins to be extracted with an aqueous solution containing at least one calixarene compound of claim 1.

12. The method of claim 11, wherein the membrane protein comprises a protein selected from the group comprising:
(a) a multi-drug efflux transporter comprising an Acridine resistance protein B (AcrB), and a proton pump comprising a bacteriorhodopsin (bR);
(b) an M2 proton channel comprising an influenza virus matrix protein 2 (M2); and
(c) an adenosine $A_{2A}$ receptor;
(d) enzymes; and
(e) glycoproteins.

13. The method of claim 11, wherein contacting the membrane pellets is effected at a pH ranging from 6 to 9.

14. The method of any of claim 11, wherein contacting the membrane pellets is effected at a temperature ranging from 4 to 25° C.

15. The method of any of claim 11, wherein contacting the membrane pellets is carried out at a calixarene concentration ranging from $10^{-6}$ to $10^{-3}$ M.

16. The method of any of claim 11, further comprising heating the membrane protein and the membrane pellets.

17. A method for producing a solution of membrane proteins, the method comprising:
- extracting membrane proteins with at least one calixarene compound of claim 1; and
- separating, by centrifugation, the membrane proteins extracted with the at least one calixarene compound.

* * * * *